US010953104B2

(12) United States Patent
Kessler et al.

(10) Patent No.: US 10,953,104 B2
(45) Date of Patent: Mar. 23, 2021

(54) DIMERIC COLLAGEN HYBRIDIZING PEPTIDES AND METHODS OF USING

(71) Applicant: UNIVERSITY OF UTAH RESEARCH FOUNDATION, Salt Lake City, UT (US)

(72) Inventors: Julian Kessler, Salt Lake City, UT (US); Michael S. Yu, Salt Lake City, UT (US); Yang Li, Salt Lake City, UT (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 0 days.

(21) Appl. No.: 15/547,504

(22) PCT Filed: Jan. 29, 2016

(86) PCT No.: PCT/US2016/015816
§ 371 (c)(1),
(2) Date: Jul. 30, 2017

(87) PCT Pub. No.: WO2016/123570
PCT Pub. Date: Aug. 4, 2016

(65) Prior Publication Data
US 2018/0000960 A1 Jan. 4, 2018

Related U.S. Application Data

(60) Provisional application No. 62/125,756, filed on Jan. 30, 2015.

(51) Int. Cl.
*A61K 47/64* (2017.01)
*C07K 14/78* (2006.01)
*A61K 47/65* (2017.01)
*G01N 33/68* (2006.01)

(52) U.S. Cl.
CPC ............ *A61K 47/641* (2017.08); *A61K 47/64* (2017.08); *A61K 47/65* (2017.08); *C07K 14/78* (2013.01); *G01N 33/6887* (2013.01); *G01N 2333/78* (2013.01); *G01N 2500/20* (2013.01)

(58) Field of Classification Search
CPC .................................................. A61K 47/641
See application file for complete search history.

(56) References Cited

U.S. PATENT DOCUMENTS

2006/0234307 A1* 10/2006 Feige ................ A61K 47/62
435/7.1
2013/0116405 A1 5/2013 Yu et al.
2013/0164220 A1* 6/2013 Yu ...................... A61K 49/0056
424/9.6
2013/0301518 A1 11/2013 Zhang et al.

FOREIGN PATENT DOCUMENTS

WO WO 2007/044026 4/2007

OTHER PUBLICATIONS

Bourguet, Benzophenone Semicarbazone Protection Strategy for Synthesis of Aza-Glycine Containing Aza-Peptides, PeptideScience 2008, 90: 824-831 (Year: 2008).*
Redman, Discovery of G-quadruplex stabilizing ligands through direct ELISA of a one-bead-one-compound library, Org. Biomol. Chem., 2006, 4, 4364-4369 (Year: 2006).*
Terao, Complex Formation of Collagen Model Peptides with Polyelectrolytes and Stabilization of the Triple Helical Structure, Macromolecules 2012, 45, 392-400 (Year: 2012).*
Redman (Discovery of G-quadruplex stabilizing ligands through direct ELISA of a one-bead-one-compound library, Org. Biomol. Chem., 2006, 4, 4364-4369, of record) (Year: 2006).*
Bourguet (Benzophenone Semicarbazone Protection Strategy for Synthesis of Aza-Glycine Containing Aza-Peptides, PeptideScience 2008, 90: 824-831, of record) (Year: 2008).*
Terao (Complex Formation of Collagen Model Peptides with Polyelectrolytes and Stabilization of the Triple Helical Structure, Macromolecules 2012, 45, 392-400, of record) (Year: 2012).*
Bella, Jordi et al., "C[alpha]-H***O=C hydrogen bonds contribute to the specificity of RGD cell-adhesion interactions.", BMC Structural Biology, vol. 5, No. 4, Feb. 14, 2005, pp. 1-13, entire document.
International Search Report and Written Opinion dated Jun. 2, 2016 for related PCT Patent Application No. PCT/US2016/015816.
Cammack, Biochemical Nomenclature Committee of IUPAC and NC-IUBMB. Newsletter 2009. Retrieved from: http://www.sbcs.qmul.ac.uk/iubmb/newsletter/2009.html#item35 (4 pages).
Default Amino Acid Abbreviations. (No Publication Date). Retrieved Apr. 28, 2018 from: http://www.alchemistmatt.com/MwtHelp/DefaultAbbreviations.htm (2 pages).
Deis, F., Amino Acid Letter Codes. Rutgers University. (No Publication Date). Retrieved Apr. 28, 2018 from: http://www.rci.rutgers.edu/~molbio/Courses/301/AA_rev.pdf (1 page).

(Continued)

Primary Examiner — Larry D Riggs, II
Assistant Examiner — Zachary J Miknis
(74) Attorney, Agent, or Firm — Ballard Spahr LLP

(57) ABSTRACT

Disclosed are peptide conjugates comprising an active agent, a spacer moiety, and a dimeric collagen hybridizing peptide comprising a first and second collagen hybridizing peptide, a linker; and a branch point, wherein the first and second collagen hybridizing peptides comprise the sequence of at least (GXY)n, wherein G is glycine, wherein X and Y are any amino acid, and wherein n is any number between 3 and 12. Also disclosed are methods of detecting denatured collagen in a sample comprising contacting a composition comprising any one of the disclosed peptide conjugates to a sample, wherein the active agent comprises a therapeutic agent, and detecting the presence or absence of binding of the peptide conjugate to denatured collagen, the presence of binding indicating the presence of denatured collagen in the sample. Also disclosed are methods of treating a disease or injury involving collagen damage comprising administering to a subject having a disease or injury involving collagen damage any one of the disclosed peptide conjugates.

20 Claims, 18 Drawing Sheets
Specification includes a Sequence Listing.

(56) References Cited

OTHER PUBLICATIONS

International Union of Pure and Applied Chemistry and International Union of Biochemistry (IUPAC-IUB). A One-Letter Notation for Amino Acid Sequences (Definitive Rules). IUPAC-IUB Commission on Biochemical Nomenclature. Butterworths. London. 1971 (6 pages). <http://iupac.org/publications/pac/pdf/1972/pdf/3104x0639.pdf>.
Non-Final Office Action dated May 3, 2018 by the U.S. Patent and Trademark Office for U.S. Appl. No. 15/331,348, filed Oct. 21, 2016 and published as US 2017/0112940 on Apr. 27, 2017 (Inventor—Yu et al.; Applicant—University of Utah Research Foundation) (3 pages).
English Translation of Office Action dated Mar. 31, 2020 by the Chinese Patent Office for Patent Application No. 2016800191222, which was filed on Jan. 29, 2016 (inventor—Kessler et al.; Applicant—University of Utah Research Foundation; (8 pages).
Communication pursuant to Article 94(3) EPC dated Apr. 7, 2020 by the European patent Office for Application No. 16744236.7, which was filed Jan. 29, 2016 (inventor—Kessler et al.; Applicant—University of Utah Research Foundation; (6 pages).
Wang, A.Y. et al., Spatio-Temporal Modification of Collagen Scaffolds Mediated by Triple Helical Propensity. Biomacromolecules. 2008; 9:1755-63.
Notice of Non-Compliant Amendment dated Sep. 7, 2018 by the U.S. Patent and Trademark Office for U.S. Appl. No. 15/331,348, filed Oct. 21, 2016 and published as US 2017/0112940 on Apr. 27, 2017 (Inventor—Yu et al.; Applicant—University of Utah Research Foundation; (4 pages).
Supplementary European Search Report dated Sep. 7, 2018 by the European Patent Office for Patent Application No. 16744236.7, which was filed on Jan. 29, 2016 and published as EP 3250240 on Dec. 6, 2017 (Inventor—Kessler et al.; Applicant—University of Utah Research Foundation; (3 pages).
Communication Pursuant to Article 94(3) EPC dated Nov. 5, 2018 by the European Patent Office for Patent Application No. 16744236.7, which was filed on Jan. 29, 2016 and published as EP 3250240 on Dec. 6, 2017 (Inventor—Kessler et al.; Applicant—University of Utah Research Foundation; (11 pages).

\* cited by examiner

```
                            SEQUENCE LISTING

<160> NUMBER OF SEQ ID NOS: 72

<210> SEQ ID NO 1
<211> LENGTH: 9
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: Xaa can be any amino acid

<400> SEQUENCE: 1

Gly Xaa Xaa Gly Xaa Xaa Gly Xaa Xaa
1               5

<210> SEQ ID NO 2
<211> LENGTH: 12
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid
```

-continued

<400> SEQUENCE: 2

Gly Xaa Xaa Gly Xaa Xaa Gly Xaa Xaa Gly Xaa Xaa
1               5                   10

<210> SEQ ID NO 3
<211> LENGTH: 15
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid
<220> FEATURE:
<221> NAME/KEY: MISC_FEATURE
<222> LOCATION: (14)..(15)
<223> OTHER INFORMATION: Xaa can be any amino acid

<400> SEQUENCE: 3

Gly Xaa Xaa Gly Xaa Xaa Gly Xaa Xaa Gly Xaa Xaa Gly Xaa Xaa
1               5                   10                  15

<210> SEQ ID NO 4
<211> LENGTH: 18
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid
<220> FEATURE:
<221> NAME/KEY: MISC_FEATURE
<222> LOCATION: (14)..(15)
<223> OTHER INFORMATION: Xaa can be any amino acid
<220> FEATURE:
<221> NAME/KEY: MISC_FEATURE
<222> LOCATION: (17)..(18)
<223> OTHER INFORMATION: Xaa can be any amino acid

<400> SEQUENCE: 4

Gly Xaa Xaa Gly Xaa Xaa Gly Xaa Xaa Gly Xaa Xaa Gly Xaa Xaa Gly
1               5                   10                  15

Xaa Xaa

```
<210> SEQ ID NO 5
<211> LENGTH: 21
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid
<220> FEATURE:
<221> NAME/KEY: MISC_FEATURE
<222> LOCATION: (14)..(15)
<223> OTHER INFORMATION: Xaa can be any amino acid
<220> FEATURE:
<221> NAME/KEY: MISC_FEATURE
<222> LOCATION: (17)..(18)
<223> OTHER INFORMATION: Xaa can be any amino acid
<220> FEATURE:
<221> NAME/KEY: MISC_FEATURE
<222> LOCATION: (20)..(21)
<223> OTHER INFORMATION: Xaa can be any amino acid

<400> SEQUENCE: 5

Gly Xaa Xaa Gly Xaa Xaa Gly Xaa Xaa Gly Xaa Xaa Gly Xaa Xaa Gly
1               5                   10                  15

Xaa Xaa Gly Xaa Xaa
            20

<210> SEQ ID NO 6
<211> LENGTH: 24
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid
<220> FEATURE:
<221> NAME/KEY: MISC_FEATURE
<222> LOCATION: (14)..(15)
<223> OTHER INFORMATION: Xaa can be any amino acid
<220> FEATURE:
<221> NAME/KEY: MISC_FEATURE
<222> LOCATION: (17)..(18)
<223> OTHER INFORMATION: Xaa can be any amino acid
<220> FEATURE:
<221> NAME/KEY: MISC_FEATURE
```

```
<222> LOCATION: (20)..(21)
<223> OTHER INFORMATION: Xaa can be any amino acid
<220> FEATURE:
<221> NAME/KEY: MISC_FEATURE
<222> LOCATION: (23)..(24)
<223> OTHER INFORMATION: Xaa can be any amino acid

<400> SEQUENCE: 6

Gly Xaa Xaa Gly Xaa Xaa Gly Xaa Xaa Gly Xaa Xaa Gly Xaa Xaa Gly
1               5                   10                  15

Xaa Xaa Gly Xaa Xaa Gly Xaa Xaa
            20

<210> SEQ ID NO 7
<211> LENGTH: 27
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid
<220> FEATURE:
<221> NAME/KEY: MISC_FEATURE
<222> LOCATION: (14)..(15)
<223> OTHER INFORMATION: Xaa can be any amino acid
<220> FEATURE:
<221> NAME/KEY: MISC_FEATURE
<222> LOCATION: (17)..(18)
<223> OTHER INFORMATION: Xaa can be any amino acid
<220> FEATURE:
<221> NAME/KEY: MISC_FEATURE
<222> LOCATION: (20)..(21)
<223> OTHER INFORMATION: Xaa can be any amino acid
<220> FEATURE:
<221> NAME/KEY: MISC_FEATURE
<222> LOCATION: (23)..(24)
<223> OTHER INFORMATION: Xaa can be any amino acid
<220> FEATURE:
<221> NAME/KEY: MISC_FEATURE
<222> LOCATION: (26)..(27)
<223> OTHER INFORMATION: Xaa can be any amino acid

<400> SEQUENCE: 7

Gly Xaa Xaa Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa
            20                  25

<210> SEQ ID NO 8
<211> LENGTH: 30
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (2)..(3)
```

```
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid
<220> FEATURE:
<221> NAME/KEY: MISC_FEATURE
<222> LOCATION: (14)..(15)
<223> OTHER INFORMATION: Xaa can be any amino acid
<220> FEATURE:
<221> NAME/KEY: MISC_FEATURE
<222> LOCATION: (17)..(18)
<223> OTHER INFORMATION: Xaa can be any amino acid
<220> FEATURE:
<221> NAME/KEY: MISC_FEATURE
<222> LOCATION: (20)..(21)
<223> OTHER INFORMATION: Xaa can be any amino acid
<220> FEATURE:
<221> NAME/KEY: MISC_FEATURE
<222> LOCATION: (23)..(24)
<223> OTHER INFORMATION: Xaa can be any amino acid
<220> FEATURE:
<221> NAME/KEY: MISC_FEATURE
<222> LOCATION: (26)..(27)
<223> OTHER INFORMATION: Xaa can be any amino acid
<220> FEATURE:
<221> NAME/KEY: MISC_FEATURE
<222> LOCATION: (29)..(30)
<223> OTHER INFORMATION: Xaa can be any amino acid

<400> SEQUENCE: 8

Gly Xaa Xaa Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa
            20                  25                  30

<210> SEQ ID NO 9
<211> LENGTH: 33
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid
<220> FEATURE:
<221> NAME/KEY: MISC_FEATURE
<222> LOCATION: (14)..(15)
<223> OTHER INFORMATION: Xaa can be any amino acid
<220> FEATURE:
<221> NAME/KEY: MISC_FEATURE
<222> LOCATION: (17)..(18)
<223> OTHER INFORMATION: Xaa can be any amino acid
<220> FEATURE:
```

```
<221> NAME/KEY: MISC_FEATURE
<222> LOCATION: (20)..(21)
<223> OTHER INFORMATION: Xaa can be any amino acid
<220> FEATURE:
<221> NAME/KEY: MISC_FEATURE
<222> LOCATION: (23)..(24)
<223> OTHER INFORMATION: Xaa can be any amino acid
<220> FEATURE:
<221> NAME/KEY: MISC_FEATURE
<222> LOCATION: (26)..(27)
<223> OTHER INFORMATION: Xaa can be any amino acid
<220> FEATURE:
<221> NAME/KEY: MISC_FEATURE
<222> LOCATION: (29)..(30)
<223> OTHER INFORMATION: Xaa can be any amino acid
<220> FEATURE:
<221> NAME/KEY: MISC_FEATURE
<222> LOCATION: (32)..(33)
<223> OTHER INFORMATION: Xaa can be any amino acid

<400> SEQUENCE: 9

Gly Xaa Xaa Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
            20                  25                  30

Xaa

<210> SEQ ID NO 10
<211> LENGTH: 36
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (2)..(3)
<223> OTHER INFORMATION: Xaa can be any amino acid
<220> FEATURE:
<221> NAME/KEY: MISC_FEATURE
<222> LOCATION: (5)..(6)
<223> OTHER INFORMATION: Xaa can be any amino acid
<220> FEATURE:
<221> NAME/KEY: MISC_FEATURE
<222> LOCATION: (8)..(9)
<223> OTHER INFORMATION: Xaa can be any amino acid
<220> FEATURE:
<221> NAME/KEY: MISC_FEATURE
<222> LOCATION: (11)..(12)
<223> OTHER INFORMATION: Xaa can be any amino acid
<220> FEATURE:
<221> NAME/KEY: MISC_FEATURE
<222> LOCATION: (14)..(15)
<223> OTHER INFORMATION: Xaa can be any amino acid
<220> FEATURE:
<221> NAME/KEY: MISC_FEATURE
<222> LOCATION: (17)..(18)
<223> OTHER INFORMATION: Xaa can be any amino acid
<220> FEATURE:
<221> NAME/KEY: MISC_FEATURE
<222> LOCATION: (20)..(21)
<223> OTHER INFORMATION: Xaa can be any amino acid
<220> FEATURE:
<221> NAME/KEY: MISC_FEATURE
<222> LOCATION: (23)..(24)
<223> OTHER INFORMATION: Xaa can be any amino acid
<220> FEATURE:
<221> NAME/KEY: MISC_FEATURE
<222> LOCATION: (26)..(27)
<223> OTHER INFORMATION: Xaa can be any amino acid
<220> FEATURE:
<221> NAME/KEY: MISC_FEATURE
<222> LOCATION: (29)..(30)
<223> OTHER INFORMATION: Xaa can be any amino acid
<220> FEATURE:
```

```
<221> NAME/KEY: MISC_FEATURE
<222> LOCATION: (32)..(33)
<223> OTHER INFORMATION: Xaa can be any amino acid
<220> FEATURE:
<221> NAME/KEY: MISC_FEATURE
<222> LOCATION: (35)..(36)
<223> OTHER INFORMATION: Xaa can be any amino acid

<400> SEQUENCE: 10

Gly Xaa Xaa Gly Xaa Xaa Gly Xaa Xaa Gly Xaa Xaa Gly Xaa Xaa Gly
1               5                   10                  15

Xaa Xaa Gly Xaa Xaa Gly Xaa Xaa Gly Xaa Xaa Gly Xaa Xaa Gly Xaa
                20                  25                  30

Xaa Gly Xaa Xaa
        35

<210> SEQ ID NO 11
<211> LENGTH: 43
<212> TYPE: PRT
<213> ORGANISM: Artificial Sequence
<220> FEATURE:
<223> OTHER INFORMATION: synthetic construct; collagen hybridizing
      peptide

<400> SEQUENCE: 11

Gly Pro Pro Gly Pro Pro Gly Pro Pro Gly Pro Pro Gly Pro Pro Gly
1               5                   10                  15

Pro Pro Gly Gly Gly Leu Gly Gly Pro Pro Gly Pro Pro Gly Pro Pro
                20                  25                  30

Pro Gly Pro Pro Gly Pro Pro Gly Pro Pro Gly
        35                  40

<210> SEQ ID NO 12
<211> LENGTH: 9
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(9)
<223> OTHER INFORMATION: Xaa can be proline, glycine, modified proline,
      or aza-glycine

<400> SEQUENCE: 12

Xaa Xaa Xaa Xaa Xaa Xaa Xaa Xaa Xaa
1               5

<210> SEQ ID NO 13
<211> LENGTH: 12
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(12)
<223> OTHER INFORMATION: Xaa can be proline, glycine, modified proline,
      or aza-glycine

<400> SEQUENCE: 13

Xaa Xaa Xaa Xaa Xaa Xaa Xaa Xaa Xaa Xaa Xaa Xaa
1               5                   10

<210> SEQ ID NO 14
```

```
<211> LENGTH: 15
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(15)
<223> OTHER INFORMATION: Xaa can be proline, glycine, modified proline,
      or aza-glycine

<400> SEQUENCE: 14

Xaa Xaa Xaa Xaa Xaa Xaa Xaa Xaa Xaa Xaa Xaa Xaa Xaa Xaa Xaa
1               5                   10                  15

<210> SEQ ID NO 15
<211> LENGTH: 18
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(18)
<223> OTHER INFORMATION: Xaa can be proline, glycine, modified proline,
      or aza-glycine

<400> SEQUENCE: 15

Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 16
<211> LENGTH: 21
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(21)
<223> OTHER INFORMATION: Xaa can be proline, glycine, modified proline,
      or aza-glycine

<400> SEQUENCE: 16

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
                20

<210> SEQ ID NO 17
<211> LENGTH: 24
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(24)
<223> OTHER INFORMATION: Xaa can be proline, glycine, modified proline,
      or aza-glycine

<400> SEQUENCE: 17

Xaa Xaa Xaa Xaa Xaa Xaa Xaa Xaa Xaa Xaa Xaa Xaa Xaa Xaa Xaa Xaa
1               5                   10                  15
```

Xaa Xaa Xaa Xaa Xaa Xaa Xaa Xaa
            20

<210> SEQ ID NO 18
<211> LENGTH: 27
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(27)
<223> OTHER INFORMATION: Xaa can be proline, glycine, modified proline,
      or aza-glycine

<400> SEQUENCE: 18

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 19
<211> LENGTH: 30
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(30)
<223> OTHER INFORMATION: Xaa can be proline, glycine, modified proline,
      or aza-glycine

<400> SEQUENCE: 19

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

<210> SEQ ID NO 20
<211> LENGTH: 33
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(33)
<223> OTHER INFORMATION: Xaa can be proline, glycine, modified proline,
      or aza-glycine

<400> SEQUENCE: 20

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa

<210> SEQ ID NO 21
<211> LENGTH: 36
<212> TYPE: PRT
<213> ORGANISM: Artificial Sequence
<220> FEATURE:
<223> OTHER INFORMATION: synthetic construct; collagen hybridizing
      peptide

```
<220> FEATURE:
<221> NAME/KEY: MISC_FEATURE
<222> LOCATION: (1)..(36)
<223> OTHER INFORMATION: Xaa can be proline, glycine, modified proline,
      or aza-glycine

<400> SEQUENCE: 21

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa
        35

<210> SEQ ID NO 22
<211> LENGTH: 39
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(39)
<223> OTHER INFORMATION: Xaa can be proline, glycine, modified proline,
      or aza-glycine

<400> SEQUENCE: 22

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa
        35

<210> SEQ ID NO 23
<211> LENGTH: 42
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(42)
<223> OTHER INFORMATION: Xaa can be proline, glycine, modified proline,
      or aza-glycine

<400> SEQUENCE: 23

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa
        35                  40

<210> SEQ ID NO 24
<211> LENGTH: 45
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(45)
<223> OTHER INFORMATION: Xaa can be proline, glycine, modified proline,
``` or aza-glycine

<400> SEQUENCE: 24

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa
        35                  40                  45

<210> SEQ ID NO 25
<211> LENGTH: 48
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(48)
<223> OTHER INFORMATION: Xaa can be proline, glycine, modified proline,
      or aza-glycine

<400> SEQUENCE: 25

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa Xaa Xaa
        35                  40                  45

<210> SEQ ID NO 26
<211> LENGTH: 51
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(51)
<223> OTHER INFORMATION: Xaa can be proline, glycine, modified proline,
      or aza-glycine

<400> SEQUENCE: 26

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa
    50

<210> SEQ ID NO 27
<211> LENGTH: 54
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(54)
<223> OTHER INFORMATION: Xaa can be proline, glycine, modified proline,
      or aza-glycine

<400> SEQUENCE: 27

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa
    50

<210> SEQ ID NO 28
<211> LENGTH: 57
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(57)
<223> OTHER INFORMATION: Xaa can be proline, glycine, modified proline,
      or aza-glycine

<400> SEQUENCE: 28

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa
    50                  55

<210> SEQ ID NO 29
<211> LENGTH: 60
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(60)
<223> OTHER INFORMATION: Xaa can be proline, glycine, modified proline,
      or aza-glycine

<400> SEQUENCE: 29

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa
    50                  55                  60

<210> SEQ ID NO 30
<211> LENGTH: 63
<212> TYPE: PRT
<213> ORGANISM: Artificial Sequence
<220> FEATURE:
<223> OTHER INFORMATION: synthetic construct; collagen hybridizing
      peptide -continued

```
<220> FEATURE:
<221> NAME/KEY: MISC_FEATURE
<222> LOCATION: (1)..(63)
<223> OTHER INFORMATION: Xaa can be proline, glycine, modified proline,
      or aza-glycine

<400> SEQUENCE: 30

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

<210> SEQ ID NO 31
<211> LENGTH: 66
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(66)
<223> OTHER INFORMATION: Xaa can be proline, glycine, modified proline,
      or aza-glycine

<400> SEQUENCE: 31

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa
65

<210> SEQ ID NO 32
<211> LENGTH: 69
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(69)
<223> OTHER INFORMATION: Xaa can be proline, glycine, modified proline,
      or aza-glycine

<400> SEQUENCE: 32

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60
```

Xaa Xaa Xaa Xaa Xaa
65

<210> SEQ ID NO 33
<211> LENGTH: 72
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(72)
<223> OTHER INFORMATION: Xaa can be proline, glycine, modified proline,
      or aza-glycine

<400> SEQUENCE: 33

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa
65                  70

<210> SEQ ID NO 34
<211> LENGTH: 75
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(75)
<223> OTHER INFORMATION: Xaa can be proline, glycine, modified proline,
      or aza-glycine

<400> SEQUENCE: 34

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa
65                  70                  75

<210> SEQ ID NO 35
<211> LENGTH: 78
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(78)
<223> OTHER INFORMATION: Xaa can be proline, glycine, modified proline,
      or aza-glycine

<400> SEQUENCE: 35

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75

<210> SEQ ID NO 36
<211> LENGTH: 81
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(81)
<223> OTHER INFORMATION: Xaa can be proline, glycine, modified proline,
      or aza-glycine

<400> SEQUENCE: 36

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa

<210> SEQ ID NO 37
<211> LENGTH: 84
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(84)
<223> OTHER INFORMATION: Xaa can be proline, glycine, modified proline,
      or aza-glycine

<400> SEQUENCE: 37

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa

```
                65                  70                  75                  80

Xaa Xaa Xaa Xaa

<210> SEQ ID NO 38
<211> LENGTH: 87
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(87)
<223> OTHER INFORMATION: Xaa can be proline, glycine, modified proline,
      or aza-glycine

<400> SEQUENCE: 38

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa
            85

<210> SEQ ID NO 39
<211> LENGTH: 90
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(90)
<223> OTHER INFORMATION: Xaa can be proline, glycine, modified proline,
      or aza-glycine

<400> SEQUENCE: 39

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa
            85                  90

<210> SEQ ID NO 40
<211> LENGTH: 93
<212> TYPE: PRT
<213> ORGANISM: Artificial Sequence
<220> FEATURE:
<223> OTHER INFORMATION: synthetic construct; collagen hybridizing
```

-continued

```
      peptide
<220> FEATURE:
<221> NAME/KEY: MISC_FEATURE
<222> LOCATION: (1)..(93)
<223> OTHER INFORMATION: Xaa can be proline, glycine, modified proline,
      or aza-glycine

<400> SEQUENCE: 40

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa
                85                  90

<210> SEQ ID NO 41
<211> LENGTH: 96
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(96)
<223> OTHER INFORMATION: Xaa can be proline, glycine, modified proline,
      or aza-glycine

<400> SEQUENCE: 41

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
                85                  90                  95

<210> SEQ ID NO 42
<211> LENGTH: 99
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(99)
<223> OTHER INFORMATION: Xaa can be proline, glycine, modified proline,
      or aza-glycine

<400> SEQUENCE: 42

Xaa Xaa Xaa Xaa Xaa Xaa Xaa Xaa Xaa Xaa Xaa Xaa Xaa Xaa Xaa
1               5                   10                  15
```

-continued

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa

<210> SEQ ID NO 43
<211> LENGTH: 102
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(102)
<223> OTHER INFORMATION: Xaa can be proline, glycine, modified proline,
      or aza-glycine

<400> SEQUENCE: 43

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa
            100

<210> SEQ ID NO 44
<211> LENGTH: 105
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(105)
<223> OTHER INFORMATION: Xaa can be proline, glycine, modified proline,
      or aza-glycine

<400> SEQUENCE: 44

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

-continued

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa
            100                 105

<210> SEQ ID NO 45
<211> LENGTH: 108
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(108)
<223> OTHER INFORMATION: Xaa can be proline, glycine, modified proline,
      or aza-glycine

<400> SEQUENCE: 45

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa
            100                 105

<210> SEQ ID NO 46
<211> LENGTH: 111
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(111)
<223> OTHER INFORMATION: Xaa can be proline, glycine, modified proline,
      or aza-glycine

<400> SEQUENCE: 46

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa

```
                65                  70                  75                  80
Xaa Xaa Xaa Xaa Xaa Xaa Xaa Xaa Xaa Xaa Xaa Xaa Xaa Xaa Xaa
                    85                  90                  95

Xaa Xaa Xaa Xaa Xaa Xaa Xaa Xaa Xaa Xaa Xaa Xaa Xaa Xaa Xaa
                   100                 105                 110

<210> SEQ ID NO 47
<211> LENGTH: 114
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(114)
<223> OTHER INFORMATION: Xaa can be proline, glycine, modified proline,
      or aza-glycine

<400> SEQUENCE: 47

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                    85                  90                  95

Xaa Xaa Xaa Xaa Xaa Xaa Xaa Xaa Xaa Xaa Xaa Xaa Xaa Xaa Xaa
                   100                 105                 110

Xaa Xaa

<210> SEQ ID NO 48
<211> LENGTH: 117
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(117)
<223> OTHER INFORMATION: Xaa can be proline, glycine, modified proline,
      or aza-glycine

<400> SEQUENCE: 48

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
```

-continued

```
                    85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa
        115

<210> SEQ ID NO 49
<211> LENGTH: 120
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(120)
<223> OTHER INFORMATION: Xaa can be proline, glycine, modified proline,
      or aza-glycine

<400> SEQUENCE: 49

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa
        100                 105                 110

Xaa Xaa Xaa Xaa Xaa Xaa Xaa Xaa
    115                 120

<210> SEQ ID NO 50
<211> LENGTH: 123
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (1)..(123)
<223> OTHER INFORMATION: Xaa can be proline, glycine, modified proline,
      or aza-glycine

<400> SEQUENCE: 50

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80
```

-continued

```
Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa
        115                 120

<210> SEQ ID NO 51
<211> LENGTH: 61
<212> TYPE: PRT
<213> ORGANISM: Artificial Sequence
<220> FEATURE:
<223> OTHER INFORMATION: synthetic construct; collagen hybridizing
      peptide

<400> SEQUENCE: 51

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Gly Gly Leu Gly
            20                  25                  30

Gly Gly Pro Pro Gly Pro Pro Gly Pro Pro Gly Pro Pro Gly Pro Pro
        35                  40                  45

Gly Pro Pro Gly Pro Pro Gly Pro Pro Gly Pro Pro Gly
    50                  55                  60

<210> SEQ ID NO 52
<211> LENGTH: 21
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (10)..(10)
<223> OTHER INFORMATION: Glycine is aza-glycine
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
<221> NAME/KEY: MISC_FEATURE
<222> LOCATION: (21)..(21)
<223> OTHER INFORMATION: Proline is hydroxyproline

<400> SEQUENCE: 52

Gly Pro Pro Gly Pro Pro Gly Pro Pro Gly Pro Pro Gly Pro Pro Gly
1               5                   10                  15

Pro Pro Gly Pro Pro
            20

<210> SEQ ID NO 53
```

```
<211> LENGTH: 21
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (5)..(5)
<223> OTHER INFORMATION: Proline is hydroxyproline
<220> FEATURE:
<221> NAME/KEY: MISC_FEATURE
<222> LOCATION: (8)..(8)
<223> OTHER INFORMATION: Proline is hydroxyproline
<220> FEATURE:
<221> NAME/KEY: MISC_FEATURE
<222> LOCATION: (11)..(11)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Glycine is aza-glycine
<220> FEATURE:
<221> NAME/KEY: MISC_FEATURE
<222> LOCATION: (14)..(14)
<223> OTHER INFORMATION: Proline is hydroxyproline
<220> FEATURE:
<221> NAME/KEY: MISC_FEATURE
<222> LOCATION: (17)..(17)
<223> OTHER INFORMATION: Proline is hydroxyproline
<220> FEATURE:
<221> NAME/KEY: MISC_FEATURE
<222> LOCATION: (20)..(20)
<223> OTHER INFORMATION: Proline is hydroxyproline

<400> SEQUENCE: 53

Pro Pro Gly Pro Pro Gly Pro Pro Gly Pro Pro Gly Pro Pro Gly Pro
1               5                   10                  15

Pro Gly Pro Pro Gly
            20

<210> SEQ ID NO 54
<211> LENGTH: 21
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (2)..(2)
<223> OTHER INFORMATION: Proline is hydroxyproline
<220> FEATURE:
<221> NAME/KEY: MISC_FEATURE
<222> LOCATION: (5)..(5)
<223> OTHER INFORMATION: Proline is hydroxyproline
<220> FEATURE:
<221> NAME/KEY: MISC_FEATURE
<222> LOCATION: (8)..(8)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Glycine is aza-glycine
<220> FEATURE:
<221> NAME/KEY: MISC_FEATURE
<222> LOCATION: (14)..(14)
<223> OTHER INFORMATION: Proline is hydroxyproline
<220> FEATURE:
<221> NAME/KEY: MISC_FEATURE
<222> LOCATION: (17)..(17)
<223> OTHER INFORMATION: Proline is hydroxyproline
<220> FEATURE:
<221> NAME/KEY: MISC_FEATURE
<222> LOCATION: (20)..(20)
<223> OTHER INFORMATION: Proline is hydroxyproline
```

<400> SEQUENCE: 54

Pro Pro Gly Pro Pro Gly Pro Pro Gly Pro Pro Gly Pro Pro Gly
1               5                   10                  15

Pro Gly Pro Pro Gly
            20

<210> SEQ ID NO 55
<211> LENGTH: 61
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
<221> NAME/KEY: MISC_FEATURE
<222> LOCATION: (21)..(21)
<223> OTHER INFORMATION: Proline is hydroxyproline
<220> FEATURE:
<221> NAME/KEY: MISC_FEATURE
<222> LOCATION: (24)..(24)
<223> OTHER INFORMATION: Proline is hydroxyproline
<220> FEATURE:
<221> NAME/KEY: MISC_FEATURE
<222> LOCATION: (27)..(27)
<223> OTHER INFORMATION: Proline is hydroxyproline
<220> FEATURE:
<221> NAME/KEY: MISC_FEATURE
<222> LOCATION: (31)..(31)
<223> OTHER INFORMATION: Lysine is a branch point and has a third
      glycine attached
<220> FEATURE:
<221> NAME/KEY: MISC_FEATURE
<222> LOCATION: (35)..(35)
<223> OTHER INFORMATION: Proline is hydroxyproline
<220> FEATURE:
<221> NAME/KEY: MISC_FEATURE
<222> LOCATION: (38)..(38)
<223> OTHER INFORMATION: Proline is hydroxyproline
<220> FEATURE:
<221> NAME/KEY: MISC_FEATURE
<222> LOCATION: (41)..(41)
<223> OTHER INFORMATION: Proline is hydroxyproline
<220> FEATURE:
<221> NAME/KEY: MISC_FEATURE
<222> LOCATION: (44)..(44)
<223> OTHER INFORMATION: Proline is hydroxyproline
<220> FEATURE:
<221> NAME/KEY: MISC_FEATURE
<222> LOCATION: (47)..(47)
<223> OTHER INFORMATION: Proline is hydroxyproline
<220> FEATURE:

```
<221> NAME/KEY: MISC_FEATURE
<222> LOCATION: (50)..(50)
<223> OTHER INFORMATION: Proline is hydroxyproline
<220> FEATURE:
<221> NAME/KEY: MISC_FEATURE
<222> LOCATION: (53)..(53)
<223> OTHER INFORMATION: Proline is hydroxyproline
<220> FEATURE:
<221> NAME/KEY: MISC_FEATURE
<222> LOCATION: (56)..(56)
<223> OTHER INFORMATION: Proline is hydroxyproline
<220> FEATURE:
<221> NAME/KEY: MISC_FEATURE
<222> LOCATION: (59)..(59)
<223> OTHER INFORMATION: Proline is hydroxyproline

<400> SEQUENCE: 55

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Gly Gly Lys Gly
                20                  25                  30

Gly Gly Pro Pro Gly Pro Pro Gly Pro Pro Gly Pro Pro Gly Pro Pro
            35                  40                  45

Gly Pro Pro Gly Pro Pro Gly Pro Pro Gly Pro Pro Gly
    50                  55                  60

<210> SEQ ID NO 56
<211> LENGTH: 27
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
<221> NAME/KEY: MISC_FEATURE
<222> LOCATION: (21)..(21)
<223> OTHER INFORMATION: Proline is hydroxyproline
<220> FEATURE:
<221> NAME/KEY: MISC_FEATURE
<222> LOCATION: (24)..(24)
<223> OTHER INFORMATION: Proline is hydroxyproline
<220> FEATURE:
<221> NAME/KEY: MISC_FEATURE
<222> LOCATION: (27)..(27)
<223> OTHER INFORMATION: Proline is hydroxyproline

<400> SEQUENCE: 56

Gly Pro Pro Gly Pro Pro Gly Pro Pro Gly Pro Pro Gly Pro Pro Gly
1               5                   10                  15
```

Pro Pro Gly Pro Pro Gly Pro Pro Gly Pro Pro
            20                  25

<210> SEQ ID NO 57
<211> LENGTH: 30
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
<221> NAME/KEY: MISC_FEATURE
<222> LOCATION: (21)..(21)
<223> OTHER INFORMATION: Proline is hydroxyproline
<220> FEATURE:
<221> NAME/KEY: MISC_FEATURE
<222> LOCATION: (24)..(24)
<223> OTHER INFORMATION: Proline is hydroxyproline
<220> FEATURE:
<221> NAME/KEY: MISC_FEATURE
<222> LOCATION: (27)..(27)
<223> OTHER INFORMATION: Proline is hydroxyproline
<220> FEATURE:
<221> NAME/KEY: MISC_FEATURE
<222> LOCATION: (30)..(30)
<223> OTHER INFORMATION: Proline is hydroxyproline

<400> SEQUENCE: 57

Gly Gly Gly Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro
            20                  25                  30

<210> SEQ ID NO 58
<211> LENGTH: 43
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE

```
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
<221> NAME/KEY: MISC_FEATURE
<222> LOCATION: (22)..(22)
<223> OTHER INFORMATION: Lysine is a branching point with a third
      glycine attached
<220> FEATURE:
<221> NAME/KEY: MISC_FEATURE
<222> LOCATION: (26)..(26)
<223> OTHER INFORMATION: Proline is hydroxyproline
<220> FEATURE:
<221> NAME/KEY: MISC_FEATURE
<222> LOCATION: (29)..(29)
<223> OTHER INFORMATION: Proline is hydroxyproline
<220> FEATURE:
<221> NAME/KEY: MISC_FEATURE
<222> LOCATION: (32)..(32)
<223> OTHER INFORMATION: Proline is hydroxyproline
<220> FEATURE:
<221> NAME/KEY: MISC_FEATURE
<222> LOCATION: (35)..(35)
<223> OTHER INFORMATION: Proline is hydroxyproline
<220> FEATURE:
<221> NAME/KEY: MISC_FEATURE
<222> LOCATION: (38)..(38)
<223> OTHER INFORMATION: Proline is hydroxyproline
<220> FEATURE:
<221> NAME/KEY: MISC_FEATURE
<222> LOCATION: (41)..(41)
<223> OTHER INFORMATION: Proline is hydroxyproline

<400> SEQUENCE: 58

Gly Pro Pro Gly Pro Pro Gly Pro Pro Gly Pro Pro Gly Pro Pro Gly
1               5                   10                  15

Pro Pro Gly Gly Gly Lys Gly Gly Gly Pro Pro Gly Pro Pro Gly Pro
            20                  25                  30

Pro Gly Pro Pro Gly Pro Pro Gly Pro Pro Gly
        35                  40

<210> SEQ ID NO 59
<211> LENGTH: 18
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
```

```
<220> FEATURE:
<221> NAME/KEY: MISC_FEATURE
<222> LOCATION: (18)..(18)
<223> OTHER INFORMATION: Proline is hydroxyproline

<400> SEQUENCE: 59

Gly Pro Pro Gly Pro Pro Gly Pro Pro Gly Pro Pro Gly Pro Pro Gly
1               5                   10                  15

Pro Pro

<210> SEQ ID NO 60
<211> LENGTH: 21
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
<221> NAME/KEY: MISC_FEATURE
<222> LOCATION: (21)..(21)
<223> OTHER INFORMATION: Proline is hydroxyproline

<400> SEQUENCE: 60

Gly Gly Gly Gly Pro Pro Gly Pro Pro Gly Pro Pro Gly Pro Pro Gly
1               5                   10                  15

Pro Pro Gly Pro Pro
            20

<210> SEQ ID NO 61
<211> LENGTH: 31
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
```

```
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
<221> NAME/KEY: MISC_FEATURE
<222> LOCATION: (21)..(21)
<223> OTHER INFORMATION: Proline is hydroxyproline
<220> FEATURE:
<221> NAME/KEY: MISC_FEATURE
<222> LOCATION: (24)..(24)
<223> OTHER INFORMATION: Proline is hydroxyproline
<220> FEATURE:
<221> NAME/KEY: MISC_FEATURE
<222> LOCATION: (27)..(27)
<223> OTHER INFORMATION: Proline is hydroxyproline

<400> SEQUENCE: 61

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Gly Gly Lys
            20                  25                  30

<210> SEQ ID NO 62
<211> LENGTH: 61
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
<221> NAME/KEY: MISC_FEATURE
<222> LOCATION: (21)..(21)
<223> OTHER INFORMATION: Proline is hydroxyproline
<220> FEATURE:
<221> NAME/KEY: MISC_FEATURE
<222> LOCATION: (24)..(24)
<223> OTHER INFORMATION: Proline is hydroxyproline
<220> FEATURE:
<221> NAME/KEY: MISC_FEATURE
<222> LOCATION: (27)..(27)
<223> OTHER INFORMATION: Proline is hydroxyproline
<220> FEATURE:
<221> NAME/KEY: MISC_FEATURE
<222> LOCATION: (31)..(31)
<223> OTHER INFORMATION: Lysine is a branch point and has a string of
      three glycines and a lysine attached
<220> FEATURE:
<221> NAME/KEY: MISC_FEATURE
<222> LOCATION: (35)..(35)
```

```
<223> OTHER INFORMATION: Proline is hydroxyproline
<220> FEATURE:
<221> NAME/KEY: MISC_FEATURE
<222> LOCATION: (38)..(38)
<223> OTHER INFORMATION: Proline is hydroxyproline
<220> FEATURE:
<221> NAME/KEY: MISC_FEATURE
<222> LOCATION: (41)..(41)
<223> OTHER INFORMATION: Proline is hydroxyproline
<220> FEATURE:
<221> NAME/KEY: MISC_FEATURE
<222> LOCATION: (44)..(44)
<223> OTHER INFORMATION: Proline is hydroxyproline
<220> FEATURE:
<221> NAME/KEY: MISC_FEATURE
<222> LOCATION: (47)..(47)
<223> OTHER INFORMATION: Proline is hydroxyproline
<220> FEATURE:
<221> NAME/KEY: MISC_FEATURE
<222> LOCATION: (50)..(50)
<223> OTHER INFORMATION: Proline is hydroxyproline
<220> FEATURE:
<221> NAME/KEY: MISC_FEATURE
<222> LOCATION: (53)..(53)
<223> OTHER INFORMATION: Proline is hydroxyproline
<220> FEATURE:
<221> NAME/KEY: MISC_FEATURE
<222> LOCATION: (56)..(56)
<223> OTHER INFORMATION: Proline is hydroxyproline
<220> FEATURE:
<221> NAME/KEY: MISC_FEATURE
<222> LOCATION: (59)..(59)
<223> OTHER INFORMATION: Proline is hydroxyproline

<400> SEQUENCE: 62

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Gly Gly Lys Gly
            20                  25                  30

Gly Gly Pro Pro Gly Pro Pro Gly Pro Pro Gly Pro Pro Gly Pro Pro
            35                  40                  45

Gly Pro Pro Gly Pro Pro Gly Pro Pro Gly Pro Pro Gly
        50                  55                  60

<210> SEQ ID NO 63
<211> LENGTH: 49
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
<221> NAME/KEY: MISC_FEATURE
<222> LOCATION: (21)..(21)
```

```
<223> OTHER INFORMATION: Proline is hydroxyproline
<220> FEATURE:
<221> NAME/KEY: MISC_FEATURE
<222> LOCATION: (25)..(25)
<223> OTHER INFORMATION: Lysine is a branch point having a third glycine
      attached
<220> FEATURE:
<221> NAME/KEY: MISC_FEATURE
<222> LOCATION: (29)..(29)
<223> OTHER INFORMATION: Proline is hydroxyproline
<220> FEATURE:
<221> NAME/KEY: MISC_FEATURE
<222> LOCATION: (32)..(32)
<223> OTHER INFORMATION: Proline is hydroxyproline
<220> FEATURE:
<221> NAME/KEY: MISC_FEATURE
<222> LOCATION: (35)..(35)
<223> OTHER INFORMATION: Proline is hydroxyproline
<220> FEATURE:
<221> NAME/KEY: MISC_FEATURE
<222> LOCATION: (38)..(38)
<223> OTHER INFORMATION: Proline is hydroxyproline
<220> FEATURE:
<221> NAME/KEY: MISC_FEATURE
<222> LOCATION: (41)..(41)
<223> OTHER INFORMATION: Proline is hydroxyproline
<220> FEATURE:
<221> NAME/KEY: MISC_FEATURE
<222> LOCATION: (44)..(44)
<223> OTHER INFORMATION: Proline is hydroxyproline

<400> SEQUENCE: 63

Gly Gly Gly Gly Pro Pro Gly Pro Pro Gly Pro Pro Gly Pro Pro Gly
1               5                   10                  15

Pro Pro Gly Pro Pro Gly Gly Gly Lys Gly Gly Gly Pro Pro Gly Pro
                20                  25                  30

Pro Gly Pro Pro Gly Pro Pro Gly Pro Pro Gly Pro Pro Gly Gly Gly
            35                  40                  45

Gly

<210> SEQ ID NO 64
<211> LENGTH: 22
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline

<400> SEQUENCE: 64
```

Gly Pro Pro Gly Pro Pro Gly Pro Pro Gly Pro Pro Gly Pro Pro Gly
1               5                   10                  15

Pro Pro Gly Gly Gly Lys
            20

<210> SEQ ID NO 65
<211> LENGTH: 43
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
<221> NAME/KEY: MISC_FEATURE
<222> LOCATION: (22)..(22)
<223> OTHER INFORMATION: Lysine is a branching point with a string of
      three glycines and a lysine attached
<220> FEATURE:
<221> NAME/KEY: MISC_FEATURE
<222> LOCATION: (26)..(26)
<223> OTHER INFORMATION: Proline is hydroxyproline
<220> FEATURE:
<221> NAME/KEY: MISC_FEATURE
<222> LOCATION: (29)..(29)
<223> OTHER INFORMATION: Proline is hydroxyproline
<220> FEATURE:
<221> NAME/KEY: MISC_FEATURE
<222> LOCATION: (32)..(32)
<223> OTHER INFORMATION: Proline is hydroxyproline
<220> FEATURE:
<221> NAME/KEY: MISC_FEATURE
<222> LOCATION: (35)..(35)
<223> OTHER INFORMATION: Proline is hydroxyproline
<220> FEATURE:
<221> NAME/KEY: MISC_FEATURE
<222> LOCATION: (38)..(38)
<223> OTHER INFORMATION: Proline is hydroxyproline
<220> FEATURE:
<221> NAME/KEY: MISC_FEATURE
<222> LOCATION: (41)..(41)
<223> OTHER INFORMATION: Proline is hydroxyproline

<400> SEQUENCE: 65

Gly Pro Pro Gly Pro Pro Gly Pro Pro Gly Pro Pro Gly Pro Pro Gly
1               5                   10                  15

Pro Pro Gly Gly Gly Lys Gly Gly Gly Pro Pro Gly Pro Pro Gly Pro
            20                  25                  30

Pro Gly Pro Pro Gly Pro Pro Gly Pro Pro Gly
            35                  40

```
<210> SEQ ID NO 66
<211> LENGTH: 43
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (10)..(10)
<223> OTHER INFORMATION: Proline is hydroxyproline
<220> FEATURE:
<221> NAME/KEY: MISC_FEATURE
<222> LOCATION: (11)..(11)
<223> OTHER INFORMATION: Proline is hydroxyproline
<220> FEATURE:
<221> NAME/KEY: MISC_FEATURE
<222> LOCATION: (13)..(13)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (22)..(22)
<223> OTHER INFORMATION: Lysine is a branching point having a string of
      three glycines and a lysine attached
<220> FEATURE:
<221> NAME/KEY: MISC_FEATURE
<222> LOCATION: (29)..(29)
<223> OTHER INFORMATION: Proline is hydroxyproline
<220> FEATURE:
<221> NAME/KEY: MISC_FEATURE
<222> LOCATION: (31)..(31)
<223> OTHER INFORMATION: Proline is hydroxyproline
<220> FEATURE:
<221> NAME/KEY: MISC_FEATURE
<222> LOCATION: (33)..(33)
<223> OTHER INFORMATION: Proline is hydroxyproline
<220> FEATURE:
<221> NAME/KEY: MISC_FEATURE
<222> LOCATION: (34)..(34)
<223> OTHER INFORMATION: Proline is hydroxyproline
<220> FEATURE:
<221> NAME/KEY: MISC_FEATURE
<222> LOCATION: (38)..(38)
<223> OTHER INFORMATION: Proline is hydroxyproline
<220> FEATURE:
<221> NAME/KEY: MISC_FEATURE
<222> LOCATION: (41)..(41)
<223> OTHER INFORMATION: Proline is hydroxyproline

<400> SEQUENCE: 66

Pro Gly Pro Pro Pro Pro Gly Gly Pro Pro Gly Pro Gly Pro Pro
1               5                   10                  15

Gly Pro Gly Gly Gly Lys Gly Gly Gly Pro Gly Pro Pro Gly Pro Gly
            20                  25                  30

Pro Pro Pro Gly Gly Pro Pro Pro Pro Gly Pro
            35                  40

<210> SEQ ID NO 67
<211> LENGTH: 15
<212> TYPE: PRT
<213> ORGANISM: Artificial Sequence
<220> FEATURE:
```

<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline

<400> SEQUENCE: 67

Gly Pro Pro Gly Pro Pro Gly Pro Pro Gly Pro Pro Gly Pro Pro
1               5                   10                  15

<210> SEQ ID NO 68
<211> LENGTH: 37
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (19)..(19)
<223> OTHER INFORMATION: Lysine is a branch point having a third glycine
      attached
<220> FEATURE:
<221> NAME/KEY: MISC_FEATURE
<222> LOCATION: (23)..(23)
<223> OTHER INFORMATION: Proline is hydroxyproline
<220> FEATURE:
<221> NAME/KEY: MISC_FEATURE
<222> LOCATION: (26)..(26)
<223> OTHER INFORMATION: Proline is hydroxyproline
<220> FEATURE:
<221> NAME/KEY: MISC_FEATURE
<222> LOCATION: (29)..(29)
<223> OTHER INFORMATION: Proline is hydroxyproline
<220> FEATURE:
<221> NAME/KEY: MISC_FEATURE
<222> LOCATION: (32)..(32)
<223> OTHER INFORMATION: Proline is hydroxyproline
<220> FEATURE:
<221> NAME/KEY: MISC_FEATURE

```
<222> LOCATION: (35)..(35)
<223> OTHER INFORMATION: Proline is hydroxyproline

<400> SEQUENCE: 68

Gly Pro Pro Gly Pro Pro Gly Pro Pro Gly Pro Pro Gly Pro Pro Gly
1               5                   10                  15

Gly Gly Lys Gly Gly Pro Pro Gly Pro Pro Gly Pro Pro Gly Pro Pro
            20                  25                  30

Pro Gly Pro Pro Gly
        35

<210> SEQ ID NO 69
<211> LENGTH: 18
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline

<400> SEQUENCE: 69

Gly Gly Gly Gly Pro Pro Gly Pro Pro Gly Pro Pro Gly Pro Pro Gly
1               5                   10                  15

Pro Pro

<210> SEQ ID NO 70
<211> LENGTH: 43
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (6)..(6)
<223> OTHER INFORMATION: Proline is hydroxyproline
<220> FEATURE:
<221> NAME/KEY: MISC_FEATURE
<222> LOCATION: (9)..(9)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
```

```
<221> NAME/KEY: MISC_FEATURE
<222> LOCATION: (22)..(22)
<223> OTHER INFORMATION: Lysine is a branch point having a third glycine
      attached
<220> FEATURE:
<221> NAME/KEY: MISC_FEATURE
<222> LOCATION: (26)..(26)
<223> OTHER INFORMATION: Proline is hydroxyproline
<220> FEATURE:
<221> NAME/KEY: MISC_FEATURE
<222> LOCATION: (29)..(29)
<223> OTHER INFORMATION: Proline is hydroxyproline
<220> FEATURE:
<221> NAME/KEY: MISC_FEATURE
<222> LOCATION: (32)..(32)
<223> OTHER INFORMATION: Proline is hydroxyproline
<220> FEATURE:
<221> NAME/KEY: MISC_FEATURE
<222> LOCATION: (35)..(35)
<223> OTHER INFORMATION: Proline is hydroxyproline
<220> FEATURE:
<221> NAME/KEY: MISC_FEATURE
<222> LOCATION: (38)..(38)
<223> OTHER INFORMATION: Proline is hydroxyproline

<400> SEQUENCE: 70

Gly Gly Gly Gly Pro Pro Gly Pro Pro Gly Pro Pro Gly Pro Pro Gly
1               5                   10                  15

Pro Pro Gly Gly Gly Lys Gly Gly Gly Pro Pro Gly Pro Pro Gly Pro
            20                  25                  30

Pro Gly Pro Pro Gly Pro Pro Gly Gly Gly Gly
            35                  40

<210> SEQ ID NO 71
<211> LENGTH: 37
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (7)..(7)
<223> OTHER INFORMATION: Proline is hydroxyproline
<220> FEATURE:
<221> NAME/KEY: MISC_FEATURE
<222> LOCATION: (8)..(8)
<223> OTHER INFORMATION: Proline is hydroxyproline
<220> FEATURE:
<221> NAME/KEY: MISC_FEATURE
<222> LOCATION: (10)..(10)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (19)..(19)
<223> OTHER INFORMATION: Lysine is a branch point having a string of
      three glycines and a lysine attached
<220> FEATURE:
<221> NAME/KEY: MISC_FEATURE
<222> LOCATION: (26)..(26)
<223> OTHER INFORMATION: Proline is hydroxyproline
<220> FEATURE:
<221> NAME/KEY: MISC_FEATURE
<222> LOCATION: (28)..(28)
<223> OTHER INFORMATION: Proline is hydroxyproline
<220> FEATURE:
<221> NAME/KEY: MISC_FEATURE
```

<222> LOCATION: (30)..(30)
<223> OTHER INFORMATION: Proline is hydroxyproline
<220> FEATURE:
<221> NAME/KEY: MISC_FEATURE
<222> LOCATION: (31)..(31)
<223> OTHER INFORMATION: Proline is hydroxyproline
<220> FEATURE:
<221> NAME/KEY: MISC_FEATURE
<222> LOCATION: (35)..(35)
<223> OTHER INFORMATION: Proline is hydroxyproline

<400> SEQUENCE: 71

Pro Pro Pro Gly Gly Pro Pro Gly Pro Gly Pro Gly Pro Gly
1               5                   10                  15

Gly Gly Lys Gly Gly Gly Pro Gly Pro Pro Gly Pro Gly Pro Pro Pro
            20                  25                  30

Gly Gly Pro Pro Pro
        35

<210> SEQ ID NO 72
<211> LENGTH: 61
<212> TYPE: PRT
<213> ORGANISM: Artificial Sequence
<220> FEATURE:
<223> OTHER INFORMATION: synthetic construct; collagen hybridizing
      peptide
<220> FEATURE:
<221> NAME/KEY: MISC_FEATURE
<222> LOCATION: (3)..(3)
<223> OTHER INFORMATION: Proline is hydroxyproline
<220> FEATURE:
<221> NAME/KEY: MISC_FEATURE
<222> LOCATION: (8)..(8)
<223> OTHER INFORMATION: Proline is hydroxyproline
<220> FEATURE:
<221> NAME/KEY: MISC_FEATURE
<222> LOCATION: (10)..(10)
<223> OTHER INFORMATION: Proline is hydroxyproline
<220> FEATURE:
<221> NAME/KEY: MISC_FEATURE
<222> LOCATION: (12)..(12)
<223> OTHER INFORMATION: Proline is hydroxyproline
<220> FEATURE:
<221> NAME/KEY: MISC_FEATURE
<222> LOCATION: (15)..(15)
<223> OTHER INFORMATION: Proline is hydroxyproline
<220> FEATURE:
<221> NAME/KEY: MISC_FEATURE
<222> LOCATION: (18)..(18)
<223> OTHER INFORMATION: Proline is hydroxyproline
<220> FEATURE:
<221> NAME/KEY: MISC_FEATURE
<222> LOCATION: (19)..(19)
<223> OTHER INFORMATION: Proline is hydroxyproline
<220> FEATURE:
<221> NAME/KEY: MISC_FEATURE
<222> LOCATION: (23)..(23)
<223> OTHER INFORMATION: Proline is hydroxyproline
<220> FEATURE:
<221> NAME/KEY: MISC_FEATURE
<222> LOCATION: (24)..(24)
<223> OTHER INFORMATION: Proline is hydroxyproline
<220> FEATURE:
<221> NAME/KEY: MISC_FEATURE
<222> LOCATION: (31)..(31)
<223> OTHER INFORMATION: Lysine is a branch point having a string of
      three glycines and a lysine attached
<220> FEATURE:
<221> NAME/KEY: MISC_FEATURE
<222> LOCATION: (38)..(38)
<223> OTHER INFORMATION: Proline is hydroxyproline
<220> FEATURE:
<221> NAME/KEY: MISC_FEATURE
<222> LOCATION: (39)..(39)
<223> OTHER INFORMATION: Proline is hydroxyproline

```
<220> FEATURE:
<221> NAME/KEY: MISC_FEATURE
<222> LOCATION: (43)..(43)
<223> OTHER INFORMATION: Proline is hydroxyproline
<220> FEATURE:
<221> NAME/KEY: MISC_FEATURE
<222> LOCATION: (44)..(44)
<223> OTHER INFORMATION: Proline is hydroxyproline
<220> FEATURE:
<221> NAME/KEY: MISC_FEATURE
<222> LOCATION: (47)..(47)
<223> OTHER INFORMATION: Proline is hydroxyproline
<220> FEATURE:
<221> NAME/KEY: MISC_FEATURE
<222> LOCATION: (50)..(50)
<223> OTHER INFORMATION: Proline is hydroxyproline
<220> FEATURE:
<221> NAME/KEY: MISC_FEATURE
<222> LOCATION: (52)..(52)
<223> OTHER INFORMATION: Proline is hydroxyproline
<220> FEATURE:
<221> NAME/KEY: MISC_FEATURE
<222> LOCATION: (54)..(54)
<223> OTHER INFORMATION: Proline is hydroxyproline
<220> FEATURE:
<221> NAME/KEY: MISC_FEATURE
<222> LOCATION: (59)..(59)
<223> OTHER INFORMATION: Proline is hydroxyproline

<400> SEQUENCE: 72

Pro Gly Pro Gly Pro Gly Pro Pro Pro Gly Pro Gly Pro Pro Pro
1               5                   10                  15

Gly Pro Pro Pro Gly Gly Pro Pro Pro Pro Gly Gly Gly Gly Lys Gly
                20                  25                  30

Gly Gly Gly Pro Pro Pro Pro Gly Gly Pro Pro Pro Gly Pro Pro Pro
            35                  40                  45

Gly Pro Gly Pro Pro Pro Pro Gly Pro Gly Pro Gly Pro
    50                  55                  60
```

DIMERIC COLLAGEN HYBRIDIZING PEPTIDES AND METHODS OF USING

CROSS-REFERENCE TO RELATED APPLICATIONS

This application is a U.S. National Phase of International Application No. PCT/US2016/015816, which was filed Jan. 29, 2016, and which claims the benefit of U.S. Provisional Application No. 62/125,756, filed Jan. 30, 2015. The content of these earlier filed applications is hereby incorporated herein by reference in theirs entirety.

STATEMENT REGARDING FEDERALLY SPONSORED RESEARCH

This invention was made with government support under R01-AR060484 and R21-AR065124 awarded by NIAMS/NIH and W81XWH-12-1-0555 awarded by DOD. The government has certain rights in the invention.

REFERENCE TO SEQUENCE LISTING

The Sequence Listing submitted Jul. 30, 2017 as a text file named "21101_0325U2 Sequence_Listing.txt," created on Jul. 28, 2017, and having a size of 71,200 bytes is hereby incorporated by reference pursuant to 37 C.F.R. § 1.52(e)(5).

BACKGROUND

Collagen is the most abundant protein in mammals, constituting approximately one third of all proteins expressed in the body and is the major component of the extracellular matrix (ECM). Defects in collagen have been shown to be associated with many pathologic conditions, including genetic diseases, arthritis, osteoporosis, cancerous tumors, and even injury to muscular skeletal tissues. Although collagen remodeling occurs during development and normal tissue maintenance, excess remodeling activity is seen in many such disease states. During collagen remodeling, native collagen triple helices are denatured and degraded by proteolytic enzymes or by mechanical stresses which exposes single-strand collagens to the surrounding ECM.

What is needed are compositions and methods for detecting degraded collagen as well as methods of targeting active agents to degraded collagen.

BRIEF SUMMARY

Disclosed are peptide conjugates comprising an active agent, a spacer moiety, and a dimeric collagen hybridizing peptide comprising a first and second collagen hybridizing peptide, a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12. In some instances, the first and second collagen hybridizing peptides can be identical. In some instances, the first and second collagen hybridizing peptides are different.

Disclosed are peptide conjugates comprising an active agent, a spacer moiety, and a dimeric collagen hybridizing peptide comprising a first and second collagen hybridizing peptide, a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein X can be proline, glutamic acid, or aspartic acid. In some instances, Y can be a modified proline, lysine, or arginine. For example, a modified proline can be hydroxyproline or fluoroproline. In some instances, the glycine can be modified as an Aza-glycine. In some instances, multiple Aza-glycines can be present.

Disclosed are peptide conjugates comprising an active agent, a spacer moiety, and a dimeric collagen hybridizing peptide comprising a first and second collagen hybridizing peptide, a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein the linker can be between the collagen hybridizing peptides and the branch point. In some instances, there can be at least two linkers. In some instances, a linker and branch point can be on the C-terminal end of the first and second collagen hybridizing peptides. In some instances, a linker and branch point can be on the N-terminal end of the first and second collagen hybridizing peptides.

Disclosed are peptide conjugates comprising an active agent, a spacer moiety, and a dimeric collagen hybridizing peptide comprising a first and second collagen hybridizing peptide, a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein the branch point can be a molecule that links the first and second collagen hybridizing peptides together through linkers attached to each first and second collagen hybridizing peptides. In some instances, a branch point attaches to a linker which can be attached to the first collagen hybridizing peptide and to a linker which can be attached to second collagen hybridizing peptide.

Disclosed are peptide conjugates comprising an active agent, a spacer moiety, and a dimeric collagen hybridizing peptide comprising a first and second collagen hybridizing peptide, a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein the dimeric peptide comprises the formula represented as (SEQ ID NO: 11)

[(Gly-Pro-Hyp)$_6$-Gly-Gly-Gly]$_2$-Lys, or (Gly-Pro-Hyp)$_6$-Gly-Gly-Gly-Lys-Gly-Gly-Gly-(Hyp-Pro-Gly)$_6$, or (Gly-Pro-Hyp)$_6$-Gly-Gly-Gly-Lys
                              /
(Gly-Pro-Hyp)$_6$-Gly-Gly-Gly

In some instances, the dimeric peptide comprises the formula represented as (SEQ ID NO: 51)

[(Gly-Pro-Hyp)$_9$-Gly-Gly-Gly]$_2$-Lys, or (Gly-Pro-Hyp)$_9$-Gly-Gly-Gly-Lys-Gly-Gly-Gly-(Hyp-Pro-Gly)$_9$, or

-continued (Gly-Pro-Hyp)₉-Gly-Gly-Gly-Lys.
/
(Gly-Pro-Hyp)₉-Gly-Gly-Gly

Disclosed are peptide conjugates comprising an active agent, a spacer moiety, and a dimeric collagen hybridizing peptide comprising a first and second collagen hybridizing peptide, a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein the active agent is a detectable moiety or a therapeutic agent. In some instances, an active agent can be attached to the N-terminal or C-terminal portion of at least one of the collagen hybridizing peptides. In some instances, a spacer moiety can be between the active agent and the first or second collagen hybridizing peptide. In some instances, an active agent can be attached to the N-terminal, C-terminal, or both portions of at least one of the collagen hybridizing peptides. In some instances, a spacer moiety can be between the active agent and the first or second collagen hybridizing.

Disclosed are methods of detecting denatured collagen in a sample comprising contacting a composition comprising any one of the disclosed peptide conjugates to a sample, wherein the active agent comprises a therapeutic agent, and detecting the presence or absence of binding of the peptide conjugate to denatured collagen, the presence of binding indicating the presence of denatured collagen in the sample.

Disclosed are methods of treating a disease or injury involving collagen damage comprising administering to a subject having a disease or injury involving collagen damage any one of the disclosed peptide conjugates.

Disclosed are kits comprising an active agent, a spacer moiety, and a dimeric collagen hybridizing peptide comprising a first and second collagen hybridizing peptide, a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12.

Disclosed are kits comprising an active agent, a first and a second collagen hybridizing peptide, a linker, and a branching moiety, wherein the first and second collagen hybridizing peptides comprise the sequence of at least (GXY)n (SEQ ID NOs:1-10), wherein G is glycine, wherein X and Y are any amino acid, and wherein n is any number between 3 and 12.

Disclosed are peptide conjugates, wherein the peptide conjugate comprises an active agent, a spacer moiety, and a dimeric collagen hybridizing peptide comprising a first and second collagen hybridizing peptide, a linker, and a branch point, wherein at least one of the first and second collagen hybridizing peptides comprises the sequence $(Xaa_1-Xaa_2-Xaa_3)n^1-Xaa_4-Xaa_5-Xaa_6-(Xaa_7-Xaa_8-Xaa_9)n^2$ (SEQ ID NOs:12-50), wherein $Xaa_1$, $Xaa_2$, $Xaa_3$, $Xaa_4$, $Xaa_5$, $Xaa_6$, $Xaa_7$, $Xaa_8$, $Xaa_9$ is glycine, proline, a modified proline or aza-glycine, and at least one of $Xaa_1$, $Xaa_2$, $Xaa_3$, $Xaa_4$, $Xaa_5$, $Xaa_6$, $Xaa_7$, $Xaa_8$, or $Xaa_9$ is aza-glycine. In some instances, no more than one of $Xaa_1$, $Xaa_2$, $Xaa_3$, $Xaa_4$, $Xaa_5$, $Xaa_6$, $Xaa_7$, $Xaa_8$, or $Xaa_9$ is aza-glycine. In some instances, $Xaa_1$, $Xaa_2$, and $Xaa_3$ are not the same amino acid. In some instances, $Xaa_4$, $Xaa_5$, and $Xaa_6$ are not the same amino acid. In some instances, $Xaa_7$, $Xaa_8$, and $Xaa_9$ are not the same amino acid. In some instances, at least two of $Xaa_1$, $Xaa_2$, and $Xaa_3$ are not the same amino acid. In some instances, at least two of $Xaa_4$, $Xaa_5$, and $Xaa_6$ are not the same amino acid. In some instances, at least two of $Xaa_7$, $Xaa_8$, and $Xaa_9$ are not the same amino acid.

Disclosed are compositions comprising one or more of the disclosed peptide conjugates.

Disclosed are nanoparticles comprising one or more of the disclosed peptide conjugates.

Additional advantages of the disclosed method and compositions will be set forth in part in the description which follows, and in part will be understood from the description, or may be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

DETAILED DESCRIPTION

Figure 1:
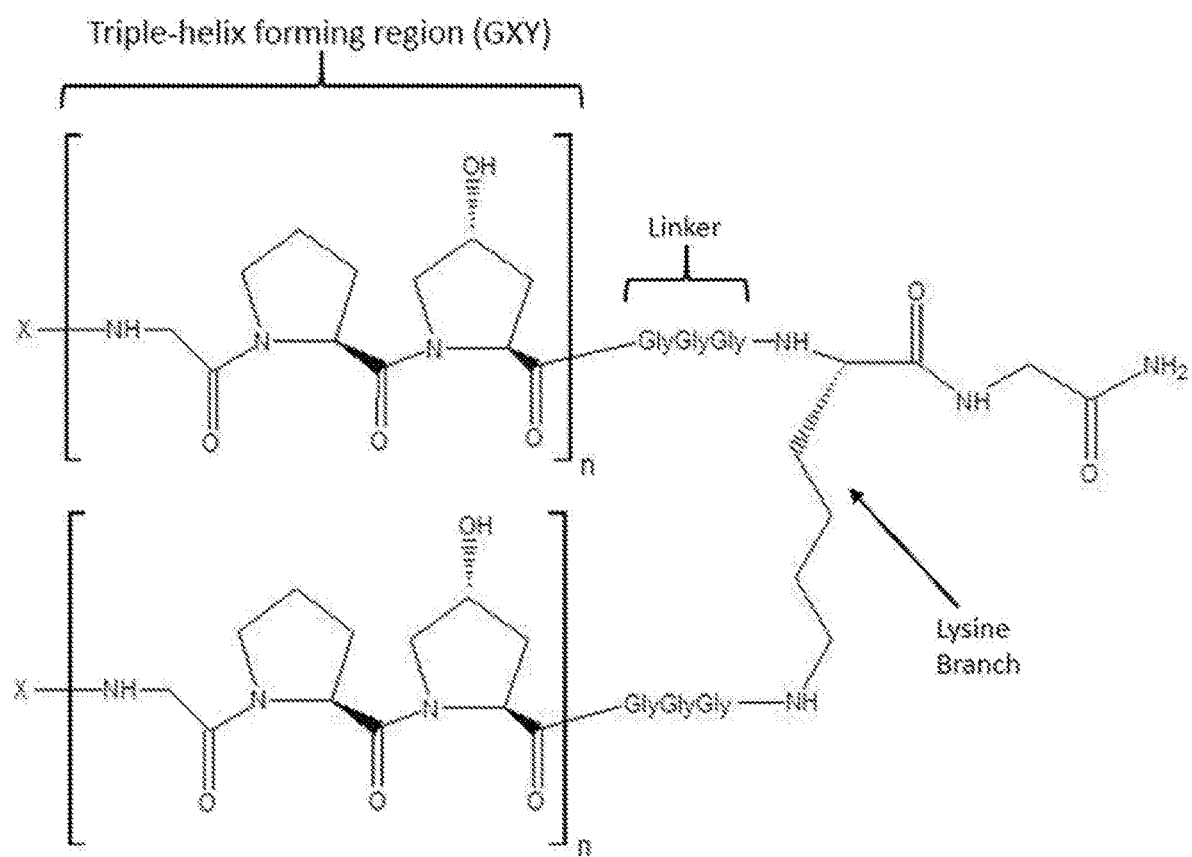
FIG. 1 shows the structure of the proposed dimeric CHP. X indicates functionalization of the N-terminus. In the case of no functionalization, X=H. The sequence shown represents SEQ ID NOs: 73-82.

The disclosed method and compositions may be understood more readily by reference to the following detailed description of particular embodiments and the Example included therein and to the Figures and their previous and following description.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a peptide conjugate is disclosed and discussed and a number of modifications that can be made to a number of molecules including the peptide conjugates are discussed, each and every combination and permutation of peptide conjugate and the modifications that are possible are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

A. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a peptide conjugate" includes a plurality of such peptide conjugates, reference to "the peptide conjugate" is a reference to one or more peptide conjugates and equivalents thereof known to those skilled in the art, and so forth.

"Optional" or "optionally" means that the subsequently described event, circumstance, or material may or may not occur or be present, and that the description includes instances where the event, circumstance, or material occurs or is present and instances where it does not occur or is not present.

The term "treating" refers to partially or completely alleviating, ameliorating, relieving, delaying onset of, inhibiting progression of, reducing severity of, and/or reducing incidence of one or more symptoms or features of a particular disease, disorder, and/or condition. For example, "treating" a disease or injury involving collagen damage can refer to reducing or eliminating the amount of damaged/denatured collagen. Treatment can also be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

The term "subject" refers to the target of administration, e.g. an animal. Thus the subject of the disclosed methods can be a vertebrate, such as a mammal. For example, the subject can be a human. The term does not denote a particular age or sex. Subject can be used interchangeably with "individual" or "patient."

Ranges may be expressed herein as from "about" one particular value, and/or to "about" another particular value. When such a range is expressed, also specifically contemplated and considered disclosed is the range¬ from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Those skilled in the art will recognize, or be able to ascertain using no more than routine experimentation, many equivalents to the specific embodiments of the method and compositions described herein. Such equivalents are intended to be encompassed by the following claims.

B. Peptide Conjugates

Disclosed are peptide conjugates comprising an active agent, a spacer moiety, and a dimeric collagen hybridizing peptide.

Disclosed are peptide conjugates comprising an active agent, a spacer moiety, and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12.

In some instances, the first and second collagen hybridizing peptides are identical. In some instances, the first and second collagen hybridizing peptides are different. In some instances, the first and second collagen hybridizing peptides can be different in the sense that the sequences are different or they can have the same sequence but the number of repeats (i.e. n) is different.

Disclosed are peptide conjugates comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein X is proline, glutamic acid, or aspartic acid.

Disclosed are peptide conjugates comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein Y is a modified proline, lysine, or arginine. In some instances, X is proline, glutamic acid, or aspartic acid and Y is a modified proline, lysine, or arginine. A modified proline can be hydroxyproline or fluoroproline.

Disclosed are peptide conjugates comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein a glycine can be modified as an Aza-glycine. In some instances, only one glycine is modified as an Aza-glycine. In some instances, at least two glycines are modified as Aza-glycines. In some aspects, the X or Y can be Aza-glycines.

Disclosed are peptide conjugates comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein the linker is between the collagen hybridizing peptides and the branch point. In some instances, there are at least two linkers. In some instances, the linker and branch point are on the C-terminal end of the first and second collagen hybridizing peptides. In some instances, the linker and branch point are on the N-terminal end of the first and second collagen hybridizing peptides. In some instances, the linker can be, but is not limited to, amino acid based or chemical. For example, the linker can be one or more glycine residues, aminohexanoic acid, or polyethylene glycol (PEG). The linker can vary depending on whether the peptides are linked at the N-terminal end or the C-terminal end. For example, for N-terminal linking a two cysteine linker can be used and for C-terminal linking a reactive end linker to a template molecule such as diacid can be used.

Disclosed are peptide conjugates comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein the branch point is a molecule that links the first and second collagen hybridizing peptides together through linkers attached to each first and second collagen hybridizing peptides. The branch point can be amino acid based or a chemical compound. For example, in some instances, the branch point can be a lysine residue. In some instances, the branch point can attach to a linker which is attached to the first collagen hybridizing peptide and to a linker which is attached to second collagen hybridizing peptide. Because the branch point attaches to a linker which attaches to the first and second collagen hybridizing peptides, the branch point is present on whichever end of the peptides the linker is located on. Thus, the branch point can be either on the N-terminal end or C-terminal end of the collagen hybridizing peptides.

Disclosed are peptide conjugates comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein n can be 6 or 9.

Disclosed are peptide conjugates comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein the dimeric peptide can be represented by the formula (SEQ ID NO: 11)

[(Gly-Pro-Hyp)₆-Gly-Gly-Gly]₂-Lys, (Gly-Pro-Hyp)₆-Gly-Gly-Gly-Lys-Gly-Gly-Gly-(Hyp-Pro-Gly)₆, or

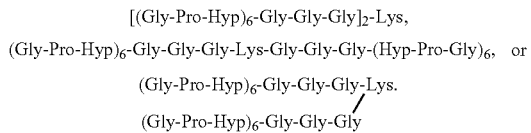

In some instances, the dimeric peptide comprises the formula (SEQ ID NO: 51)

[(Gly-Pro-Hyp)₉-Gly-Gly-Gly]₂-Lys, (Gly-Pro-Hyp)₉-Gly-Gly-Gly-Lys-Gly-Gly-Gly-(Hyp-Pro-Gly)₉, or

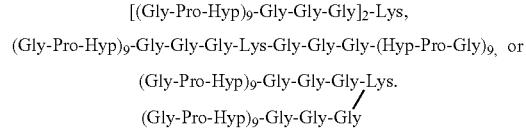

Disclosed are peptide conjugates comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein the dimeric collagen hybridizing peptide can be attached to a solid support. In some instances, the solid support can be attached via an attachment point present between the branch point and the solid support. In some instances, the attachment point can be any amino acid residue. In some instances, the branch point also serves as the attachment point for the solid support. For example, the attachment point can be a glycine residue. In some instances, solid supports can be, but are not limited to, resin, polymeric beads, agarose beads, nanotubes, nanoparticles, surface coated with gold, acrylamide, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumarate, collagen, glycosaminoglycans, and polyamino acids or any polymeric surface. Solid supports can have any useful form including thin films or membranes, beads, bottles, dishes, fibers, optical fibers, woven fibers, chips, compact disks, shaped polymers, metals, particles and microparticles. A chip is a rectangular or square small piece of material.

Disclosed are peptide conjugates comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein the active agent can be a detectable moiety or a therapeutic agent. In some instances, the active agent can be attached to the N-terminal or C-terminal portion of at least one of the collagen hybridizing peptides. In some instances, an active agent can be attached to only one of the collagen hybridizing peptides. In some instances, an active agent can be attached to both of the collagen hybridizing peptides. In some instances, an active agent can be present at both the N-terminal and C-terminal ends of one or both of the collagen hybridizing peptides.

In some instances, the detectable moiety can be a fluorescent dye, radioactive isotope, magnetic bead, metallic bead, colloidal particle, near-infrared dye, or an electron-dense reagent. Thus, detectable moieties can be, but are not limited to, fluorescent moieties, radioactive moieties, electronic moieties, and indirect moieties such as biotin or digoxigenin. When indirect moieties are used, a secondary binding agent that binds the indirect moiety can be used to detect the presence of a bound collagen hybridizing peptide. These secondary binding agents can comprise antibodies, haptens, or other binding partners (e.g., avidin) that bind to the indirect moieties.

In some instances, the therapeutic agent can be a therapeutic known to treat a disease or injury involving collagen damage. For example, the therapeutic agent can be, but is not limited to, any suitable pharmaceutical or other therapeutic agent, including but not limited to, osteogenic promoters, antimicrobials, anti-inflammatory agents, polypeptides such as recombinant proteins, cytokines or antibodies, small molecule chemicals or any combination thereof. In some instances, a therapeutic agent can be a cancer drug, arthritis drug or osteoporosis drug. Therapeutic agents can be capable of promoting bone growth, decreasing inflammation, promoting collagen stability. The therapeutic agent can include, but is not limited to, bone morphogenic protein (BMP), G-CSF, FGF, BMP-2, BMP-3, FGF-2, FGF-4, anti-sclerostin antibody, growth hormone, IGF-1, VEGF, TGF-.beta., KGF, FGF-10, TGF-.alpha., TGF-.beta.1, TGF-.beta. receptor, CT, GH, GM-CSF, EGF, PDGF, celiprolol, activins and connective tissue growth factors. In some instances, a therapeutic agent can be an antibody such as, but not limited to, Avastin, Eylea, Humira, ReoPro, Campath, tocilizumab, Ilaris, Removab, Cimzia, Erbitux, Zenapax, Prolia, Raptiva, Rexomun, Abegrin, HuZAF, Simponi, Igovomab, IMAB362, Imciromab, Remicade, Yervoy, Tysabri, Theracim, OvaRex, Vectibix, Theragyn, Omnitarg, Cyramza, Lucentis, Antova, Actemra, Herceptin, Ektomab, Stelara, HumaSPECT, HuMax-EGFr, HuMax-CD4. A therapeutic agent can target tumors, arthritis, osteoporosis, MMP inhibitors, cathepsin inhibitors, interleukin inhibitors, TRAIL inhibitors, VEGF inhibitors, or CD binding agents.

In some instances, a disease or injury involving collagen damage can be, but is not limited to, cartilage/bone injury, tendon/ligament injury, corneal injury, and disease with high collagen remodeling activity such as cancer, arthritis, osteoporosis, fibrosis, and vulnerable plaques.

Disclosed are peptide conjugates comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, wherein the spacer moiety can be between the active agent and the first or second collagen hybridizing. In some instances, the spacer moiety can comprise aminohexanoic acid. In some instances, the spacer moiety can be one or more glycines or PEG.

Also disclosed are peptide conjugates, wherein the peptide conjugate comprises an active agent, a spacer moiety, and a dimeric collagen hybridizing peptide comprising a first and second collagen hybridizing peptide, a linker, and a branch point, wherein at least one of the first and second collagen hybridizing peptides comprises the sequence $(Xaa_1-Xaa_2-Xaa_3)n^1-Xaa_4-Xaa_5-Xaa_6-(Xaa_7-Xaa_8-Xaa_9)n^2$ (SEQ ID NOs:12-50), wherein $Xaa_1$, $Xaa_2$, $Xaa_3$, $Xaa_4$, $Xaa_5$, $Xaa_6$, $Xaa_7$, $Xaa_8$, $Xaa_9$ is glycine, proline, a modified proline or aza-glycine, and at least one of $Xaa_1$, $Xaa_2$, $Xaa_3$, $Xaa_4$, $Xaa_5$, $Xaa_6$, $Xaa_7$, $Xaa_8$, or $Xaa_9$ is aza-glycine. In some instances, wherein no more than one of $Xaa_1$, $Xaa_2$, $Xaa_3$, $Xaa_4$, $Xaa_5$, $Xaa_6$, $Xaa_7$, $Xaa_8$, or $Xaa_9$ can be aza-glycine. In some instances, $Xaa_1$, $Xaa_2$, and $Xaa_3$ are not the same amino acid. In some instances, $Xaa_4$, $Xaa_5$, and $Xaa_6$ are not the same amino acid. In some instances, $Xaa_7$, $Xaa_8$, and $Xaa_9$ are not the same amino acid. In some instances, at least two of $Xaa_1$, $Xaa_2$, and $Xaa_3$ are not the same amino acid. In some instances, at least two of $Xaa_4$, $Xaa_5$, and $Xaa_6$ are not the same amino acid. In some instances, at least two of $Xaa_7$, $Xaa_8$, and $Xaa_9$ are not the same amino acid.

Disclosed are peptide conjugates, wherein the peptide conjugate comprises an active agent, a spacer moiety, and a dimeric collagen hybridizing peptide comprising a first and second collagen hybridizing peptide, a linker, and a branch point, wherein at least one of the first and second collagen hybridizing peptides comprises the sequence $(Xaa_1-Xaa_2-Xaa_3)n^1-Xaa_4-Xaa_5-Xaa_6-(Xaa_7-Xaa_8-Xaa_9)n^2$ (SEQ ID NOs:12-50), wherein $Xaa_1$, $Xaa_2$, $Xaa_3$, $Xaa_4$, $Xaa_5$, $Xaa_6$, $Xaa_7$, $Xaa_8$, $Xaa_9$ is glycine, proline, a modified proline or aza-glycine, and at least one of $Xaa_1$, $Xaa_2$, $Xaa_3$, $Xaa_4$, $Xaa_5$, $Xaa_6$, $Xaa_7$, $Xaa_8$, or $Xaa_9$ is aza-glycine, wherein the peptides comprise the sequence (Gly-Pro-Hyp)$_3$-azGly-Pro-Hyp-(Gly-Pro-Hyp)$_3$ (SEQ ID NO:52), (Pro-Hyp-Gly)$_3$-

Pro-Hyp-azGly-(Pro-Hyp-Gly)$_3$ (SEQ ID NO:53), or (Pro-Hyp-Gly)$_3$-Pro-Pro-azGly-(Pro-Hyp-Gly)$_3$ (SEQ ID NO:54).

Disclosed are peptide conjugates, wherein the peptide conjugate comprises an active agent, a spacer moiety, and a dimeric collagen hybridizing peptide comprising a first and second collagen hybridizing peptide, a linker, and a branch point, wherein at least one of the first and second collagen hybridizing peptides comprises the sequence (Xaa$_1$-Xaa$_2$-Xaa$_3$)n$^1$-Xaa$_4$-Xaa$_5$-Xaa$_6$-(Xaa$_7$-Xaa$_8$-Xaa$_9$)n$^2$ (SEQ ID NOs:12-50), wherein Xaa$_1$, Xaa$_2$, Xaa$_3$, Xaa$_4$, Xaa$_5$, Xaa$_6$, Xaa$_7$, Xaa$_8$, Xaa$_9$ is glycine, proline, a modified proline or aza-glycine, and at least one of Xaa$_1$, Xaa$_2$, Xaa$_3$, Xaa$_4$, Xaa$_5$, Xaa$_6$, Xaa$_7$, Xaa$_8$, or Xaa$_9$ is aza-glycine, wherein n$^1$ can be an integer from 1 to 20. In some instances, n$^2$ can be an integer from 1 to 20.

Disclosed are peptide conjugates, wherein the peptide conjugate comprises an active agent, a spacer moiety, and a dimeric collagen hybridizing peptide comprising a first and second collagen hybridizing peptide, a linker, and a branch point, wherein at least one of the first and second collagen hybridizing peptides comprises the sequence (Xaa$_1$-Xaa$_2$-Xaa$_3$)n$^1$-Xaa$_4$-Xaa$_5$-Xaa$_6$-(Xaa$_7$-Xaa$_8$-Xaa$_9$)n$^2$ (SEQ ID NOs:12-50), wherein Xaa$_1$, Xaa$_2$, Xaa$_3$, Xaa$_4$, Xaa$_5$, Xaa$_6$, Xaa$_7$, Xaa$_8$, Xaa$_9$ is glycine, proline, a modified proline or aza-glycine, and at least one of Xaa$_1$, Xaa$_2$, Xaa$_3$, Xaa$_4$, Xaa$_5$, Xaa$_6$, Xaa$_7$, Xaa$_8$, or Xaa$_9$ is aza-glycine, wherein the active agent can be a detectable moiety or a therapeutic agent. In some instances, a detectable moiety can be a fluorescent dye, radioactive isotope, magnetic bead, metallic bead, colloidal particle, near-infra red dye, or an electron-dense reagents. Thus, detectable moieties can be, but are not limited to, fluorescent moieties, radioactive moieties, electronic moieties, and indirect moieties such as biotin or digoxigenin. When indirect moieties are used, a secondary binding agent that binds the indirect moiety can be used to detect the presence of a bound collagen hybridizing peptide. These secondary binding agents can comprise antibodies, haptens, or other binding partners (e.g., avidin) that bind to the indirect moieties. In some instances, a detectable moiety can be attached to the N-terminal, C-terminal, or both portions of the peptide. In some instances, the therapeutic agent can be a therapeutic known to treat a disease or injury involving collagen damage. For example, the therapeutic agent can be, but is not limited to, any suitable pharmaceutical or other therapeutic agent, including but not limited to, osteogenic promoters, antimicrobials, anti-inflammatory agents, polypeptides such as recombinant proteins, cytokines or antibodies, small molecule chemicals or any combination thereof. In some instances, a therapeutic agent can be a cancer drug, arthritis drug or osteoporosis drug. Therapeutic agents can be capable of promoting bone growth, decreasing inflammation, promoting collagen stability. Examples of therapeutic agents can include, but is not limited to, bone morphogenic protein (BMP), G-CSF, FGF, BMP-2, BMP-3, FGF-2, FGF-4, anti-sclerostin antibody, growth hormone, IGF-1, VEGF, TGF-β, KGF, FGF-10, TGF-α, TGF-β1, TGF-β receptor, CT, GH, GM-CSF, EGF, PDGF, celiprolol, activins and connective tissue growth factors. In some instances, a therapeutic agent can be an antibody such as, but not limited to, Avastin, Eylea, Humira, ReoPro, Campath, tocilizumab, Ilaris, Removab, Cimzia, Erbitux, Zenapax, Prolia, Raptiva, Rexomun, Abegrin, HuZAF, Simponi, Igovomab, IMAB362, Imciromab, Remicade, Yervoy, Tysabri, Theracim, OvaRex, Vectibix, Theragyn, Omnitarg, Cyramza, Lucentis, Antova, Actemra, Herceptin, Ektomab, Stelara, HumaSPECT, HuMax-EGFr, HuMax-CD4. A therapeutic agent can target tumors, arthritis, osteoporosis, MMP inhibitors, cathepsin inhibitors, interleukin inhibitors, TRAIL inhibitors, VEGF inhibitors, or CD binding agents.

In some instances, a disease or injury involving collagen damage can be, but is not limited to, cartilage/bone injury, tendon/ligament injury, corneal injury, and disease with high collagen remodeling activity such as cancer, arthritis, osteoporosis, fibrosis, and vulnerable plaques.

Disclosed are peptide conjugates, wherein the peptide conjugate comprises an active agent, a spacer moiety, and a dimeric collagen hybridizing peptide comprising a first and second collagen hybridizing peptide, a linker, and a branch point, wherein at least one of the first and second collagen hybridizing peptides comprises the sequence (Xaa$_1$-Xaa$_2$-Xaa$_3$)n$^1$-Xaa$_4$-Xaa$_5$-Xaa$_6$-(Xaa$_7$-Xaa$_8$-Xaa$_9$)n$^2$ (SEQ ID NOs:12-50), wherein Xaa$_1$, Xaa$_2$, Xaa$_3$, Xaa$_4$, Xaa$_5$, Xaa$_6$, Xaa$_7$, Xaa$_8$, Xaa$_9$ is glycine, proline, a modified proline or aza-glycine, and at least one of Xaa$_1$, Xaa$_2$, Xaa$_3$, Xaa$_4$, Xaa$_5$, Xaa$_6$, Xaa$_7$, Xaa$_8$, or Xaa$_9$ is aza-glycine, wherein the spacer moiety is located between the active agent and the peptide. In some instances, the spacer moiety can comprise aminohexanoic acid. In some instances, the spacer moiety can be one or more glycines or PEG.

Disclosed are peptide conjugates, wherein the peptide conjugate comprises an active agent, a spacer moiety, and a dimeric collagen hybridizing peptide comprising a first and second collagen hybridizing peptide, a linker, and a branch point, wherein at least one of the first and second collagen hybridizing peptides comprises the sequence (Xaa$_1$-Xaa$_2$-Xaa$_3$)n$^1$-Xaa$_4$-Xaa$_5$-Xaa$_6$-(Xaa$_7$-Xaa$_8$-Xaa$_9$)n$^2$ (SEQ ID NOs:12-50), wherein Xaa$_1$, Xaa$_2$, Xaa$_3$, Xaa$_4$, Xaa$_5$, Xaa$_6$, Xaa$_7$, Xaa$_8$, Xaa$_9$ is glycine, proline, a modified proline or aza-glycine, and at least one of Xaa$_1$, Xaa$_2$, Xaa$_3$, Xaa$_4$, Xaa$_5$, Xaa$_6$, Xaa$_7$, Xaa$_8$, or Xaa$_9$ is aza-glycine, wherein the peptides have a higher affinity to degraded collagen than a conventional collagen hybridizing peptide. In some instances, the peptides do not bind native collagen.

C. Compositions

Disclosed are compositions comprising one or more of the disclosed peptide conjugates. In some instances, the disclosed compositions further comprise a pharmaceutically acceptable carrier. For example, disclosed are compositions comprising one or more peptide conjugates, wherein the peptide conjugates comprise an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12. Also disclosed compositions comprising one or more peptide conjugates, wherein the peptide conjugate comprises an active agent, a spacer moiety, and a dimeric collagen hybridizing peptide comprising a first and second collagen hybridizing peptide, a linker, and a branch point, wherein at least one of the first and second collagen hybridizing peptides comprises the sequence (Xaa$_1$-Xaa$_2$-Xaa$_3$)n$^1$-Xaa$_4$-Xaa$_5$-Xaa$_6$-(Xaa$_7$-Xaa$_8$-Xaa$_9$)n$^2$ (SEQ ID NOs:12-50), wherein Xaa$_1$, Xaa$_2$, Xaa$_3$, Xaa$_4$, Xaa$_5$, Xaa$_6$, Xaa$_7$, Xaa$_8$, Xaa$_9$ is glycine, proline, a modified proline or aza-glycine, and at least one of Xaa$_1$, Xaa$_2$, Xaa$_3$, Xaa$_4$, Xaa$_5$, Xaa$_6$, Xaa$_7$, Xaa$_8$, or Xaa$_9$ is aza-glycine.

For example, the compositions described herein can comprise a pharmaceutically acceptable carrier. By "pharmaceutically acceptable" is meant a material or carrier that would be selected to minimize any degradation of the active ingredient and to minimize any adverse side effects in the subject, as would be well known to one of skill in the art. Examples of carriers include dimyristoylphosphatidyl (DMPC), phosphate buffered saline or a multivesicular liposome. For example, PG:PC:Cholesterol:peptide or PC:peptide can be used as carriers in this invention. Other suitable pharmaceutically acceptable carriers and their formulations are described in Remington: The Science and Practice of Pharmacy (19th ed.) ed. A.R. Gennaro, Mack Publishing Company, Easton, Pa. 1995. Typically, an appropriate amount of pharmaceutically-acceptable salt is used in the formulation to render the formulation isotonic. Other examples of the pharmaceutically-acceptable carrier include, but are not limited to, saline, Ringer's solution and dextrose solution. The pH of the solution can be from about 5 to about 8, or from about 7 to about 7.5. Further carriers include sustained release preparations such as semi-permeable matrices of solid hydrophobic polymers containing the composition, which matrices are in the form of shaped articles, e.g., films, stents (which are implanted in vessels during an angioplasty procedure), liposomes or microparticles. It will be apparent to those persons skilled in the art that certain carriers may be more preferable depending upon, for instance, the route of administration and concentration of composition being administered. These most typically would be standard carriers for administration of drugs to humans, including solutions such as sterile water, saline, and buffered solutions at physiological pH.

Pharmaceutical compositions can also include carriers, thickeners, diluents, buffers, preservatives and the like, as long as the intended activity of the polypeptide, peptide, or conjugate of the invention is not compromised. Pharmaceutical compositions may also include one or more active ingredients (in addition to the composition of the invention) such as antimicrobial agents, anti-inflammatory agents, anesthetics, and the like.

D. Nanoparticles

Disclosed are nanoparticles comprising one or more of the disclosed peptide conjugates. Thus, disclosed are nanoparticles comprising one or more peptide conjugate, wherein the one or more peptide conjugate comprises an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12.

Also disclosed are nanoparticles comprising one or more peptide conjugate, wherein the one or more peptide conjugate comprises an active agent, a spacer moiety, and a dimeric collagen hybridizing peptide comprising a first and second collagen hybridizing peptide, a linker, and a branch point, wherein at least one of the first and second collagen hybridizing peptides comprises the sequence $(Xaa_1-Xaa_2-Xaa_3)n^1-Xaa_4-Xaa_5-Xaa_6-(Xaa_7-Xaa_8-Xaa_9)n^2$ (SEQ ID NOs:12-50), wherein $Xaa_1$, $Xaa_2$, $Xaa_3$, $Xaa_4$, $Xaa_5$, $Xaa_6$, $Xaa_7$, $Xaa_8$, $Xaa_9$ is glycine, proline, a modified proline or aza-glycine, and at least one of $Xaa_1$, $Xaa_2$, $Xaa_3$, $Xaa_4$, $Xaa_5$, $Xaa_6$, $Xaa_7$, $Xaa_8$, or $Xaa_9$ is aza-glycine.

Nanoparticles generally refers to particles in the range of between 500 nm to less than 0.5 nm. In some instances, nanoparticles can have a diameter that is between 50 and 500 nm. In some instances, nanoparticles can have a diameter that is between 50 and 300 nm. Cellular internalization of polymeric particles is highly dependent upon their size, with nanoparticulate polymeric particles being internalized by cells with much higher efficiency than micoparticulate polymeric particles. For example, Desai, et al. have demonstrated that about 2.5 times more nanoparticles that are 100 nm in diameter are taken up by cultured Caco-2 cells as compared to microparticles having a diameter on 1 μM (Desai, et al., Pharm. Res., 14:1568-73 (1997)). Nanoparticles can also diffuse deeper into tissues in vivo.

Polymers can form the core of nanoparticles and can be any biodegradable or non-biodegradable synthetic or natural polymer. In some instances, the polymer is a biodegradable polymer. Nanoparticles are ideal materials as delivery vehicles as they are efficient at passing through biological barriers and can be used for sustained release of encapsulated, genetic variant over a period in the range of days to months by varying factors such as the monomer ratios or polymer size, for example, poly(lactic acid) (PLA) to poly (glycolic acid) (PGA) copolymer ratios.

Examples of preferred biodegradable polymers include synthetic polymers that degrade by hydrolysis such as poly(hydroxy acids), such as polymers and copolymers of lactic acid and glycolic acid, polyanhydrides, poly(ortho) esters, polyesters, polyurethanes, poly(butic acid), poly(valeric acid), poly(caprolactone), poly(hydroxyalkanoates), and poly(lactide-co-caprolactone).

Natural polymers can include alginate and other polysaccharides, collagen, albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

In some instances, non-biodegradable polymers can be used, especially hydrophobic polymers. Examples of non-biodegradable polymers include ethylene vinyl acetate, poly (meth) acrylic acid, copolymers of maleic anhydride with other unsaturated polymerizable monomers, poly(butadiene maleic anhydride), polyamides, copolymers and mixtures thereof, and dextran, cellulose and derivatives thereof.

Other suitable biodegradable and non-biodegradable polymers include, but are not limited to, polyanhydrides, polyamides, polycarbonates, polyalkylenes, polyalkylene oxides such as polyethylene glycol, polyalkylene terephthalates such as poly(ethylene terephthalate), polyvinyl alcohols, polyvinyl ethers, polyvinyl esters, polyethylene, polypropylene, polyvinyl acetate), poly vinyl chloride, polystyrene, polyvinyl halides, polyvinylpyrrolidone, polymers of acrylic and methacrylic esters, polysiloxanes, polyurethanes and copolymers thereof, modified celluloses, alkyl cellulose, hydroxyalkyl celluloses, cellulose ethers, cellulose esters, nitro celluloses, cellulose acetate, cellulose propionate, cellulose acetate butyrate, cellulose acetate phthalate, carboxyethyl cellulose, cellulose triacetate, cellulose sulfate sodium salt, and polyacrylates such as poly(methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate). These materials can be used alone, as physical mixtures (blends), or as co-polymers.

The polymer may be a bioadhesive polymer that is hydrophilic or hydrophobic. Hydrophilic polymers include CARBOPOL™ (a high molecular weight, crosslinked, acrylic acid-based polymers manufactured by NOVEON™), polycarbophil, cellulose esters, and dextran.

Release rate controlling polymers can be included in the polymer matrix or in the coating on the formulation. Examples of rate controlling polymers that may be used are hydroxypropylmethylcellulose (HPMC) with viscosities of either 5, 50, 100 or 4000 cps or blends of the different viscosities, ethylcellulose, methylmethacrylates, such as EUDRAGIT® RS100, EUDRAGIT® RL100, EUDRAGIT NE 30D (supplied by Rohm America). Gastrosoluble polymers, such as EUDRAGIT® E100 or enteric polymers such as EUDRAGIT® L100-55D, L100 and S100 may be blended with rate controlling polymers to achieve pH dependent release kinetics. Other hydrophilic polymers such as alginate, polyethylene oxide, carboxymethylcellulose, and hydroxyethylcellulose may be used as rate controlling polymers.

E. Methods of Screening and Detecting

Disclosed are methods of detecting denatured collagen in a sample comprising contacting a composition comprising any one of the disclosed peptide conjugates to a sample, wherein the active agent comprises a therapeutic agent, detecting the presence or absence of binding of the peptide conjugate to denatured collagen, the presence of binding indicating the presence of denatured collagen in the sample. For example, disclosed are methods of detecting denatured collagen in a sample comprising contacting a composition comprising a peptide conjugate comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12 to a sample, wherein the active agent comprises a therapeutic agent, detecting the presence or absence of binding of the peptide conjugate to denatured collagen, the presence of binding indicating the presence of denatured collagen in the sample. In some instances, the absence of binding indicates the absence of denatured collagen in the sample.

In some instances, the presence of binding can be determined using an immunoassay, a fluorescence assay or an enzyme-based assay. Thus, in some instances, detectable moieties can be, but are not limited to, can be a fluorescent dye, radioactive isotope, magnetic bead, metallic bead, colloidal particle, near-infrared dye, or an electron-dense reagent. Thus, detectable moieties can be, but are not limited to, fluorescent moieties, radioactive moieties, electronic moieties, and indirect moieties such as biotin or digoxigenin. When indirect moieties are used, a secondary binding agent that binds the indirect moiety can be used to detect the presence of a bound collagen hybridizing peptide. These secondary binding agents can comprise antibodies, haptens, or other binding partners (e.g., avidin) that bind to the indirect moieties.

Also disclosed are methods of screening for a therapeutic agent that treats a disease or injury involving collagen damage. In some instances, a disease or injury involving collagen damage can be, but is not limited to, cartilage/bone injury, tendon/ligament injury, corneal injury, and disease with high collagen remodeling activity such as cancer, arthritis, osteoporosis, fibrosis, and vulnerable plaques. The screening methods include detecting damaged or denatured collagen in a sample, administering a therapeutic to the sample, and then detecting the presence of the damaged or denatured collagen again. If the presence of damaged or denatured collagen has reduced then the therapeutic agent is an effective treatment for a disease or injury involving collagen damage. If the presence of damaged or denatured collagen stays the same or increases then the therapeutic agent is not an effective treatment for a disease or injury involving collagen damage.

Disclosed are method of screening for a therapeutic agent that treats a disease or injury involving collagen damage comprising detecting the presence or absence of binding of the peptide conjugate to denatured collagen, the presence of binding indicating the presence of denatured collagen in the sample, administering to a sample having denatured collagen a composition comprising any one of the disclosed peptide conjugates, and detecting the presence or absence of binding of the peptide conjugate to denatured collagen, the presence of binding indicating the presence of denatured collagen in the sample, wherein a decrease in the amount of damaged or denatured collagen in the sample detected after administration of the peptide conjugate compared to the amount detected prior to administration of the peptide conjugate indicates a therapeutic agent capable of a disease or injury involving collagen damage. In some instances, detecting the presence or absence of binding of the peptide conjugate to denatured collagen comprises contacting a composition comprising any one of the disclosed peptide conjugates to a sample, wherein the presence of binding can be determined using an immunoassay, a fluorescence assay or an enzyme-based assay.

Disclosed are method of screening for a therapeutic agent that treats a disease or injury involving collagen damage comprising detecting the presence or absence of binding of the peptide conjugate to denatured collagen, the presence of binding indicating the presence of denatured collagen in the sample, administering to a sample having denatured collagen a composition comprising a peptide conjugate comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12, and detecting the presence or absence of binding of the peptide conjugate to denatured collagen, the presence of binding indicating the presence of denatured collagen in the sample, wherein a decrease in the amount of damaged or denatured collagen in the sample detected after administration of the peptide conjugate compared to the amount detected prior to administration of the peptide conjugate indicates a therapeutic agent capable of a disease or injury involving collagen damage.

F. Methods of Treating

Disclosed are methods of treating a disease or injury involving collagen damage comprising administering to a subject having a disease or injury involving collagen damage any of the disclosed peptide conjugates. In some instances, a disease or injury involving collagen damage can be, but is not limited to, cartilage/bone injury, tendon/ligament injury, corneal injury, and disease with high collagen remodeling activity such as cancer, arthritis, osteoporosis, fibrosis, and vulnerable plaques.

Disclosed are methods of treating a disease or injury involving collagen damage comprising detecting the presence or absence of binding of the peptide conjugate to denatured or damaged collagen, the presence of binding indicating the presence of denatured collagen in the sample, administering to a sample having denatured collagen a composition comprising any one of the disclosed peptide conjugates. In some instances, detecting the presence or absence of binding of the peptide conjugate to denatured collagen comprises contacting a composition comprising any one of the disclosed peptide conjugates to a sample and detecting the binding of the peptide conjugate to damaged or denatured collagen in the sample. In some instances, the presence of binding can be determined using an immunoassay, a fluorescence assay or an enzyme-based assay.

Disclosed are methods of treating a disease or injury involving collagen damage comprising administering to a sample a composition comprising any one of the disclosed peptide conjugates, detecting the presence or absence of binding of the peptide conjugate to denatured or damaged collagen, the presence of binding indicating the presence of denatured collagen in the sample, treating the sample having denatured or damaged collagen with a composition comprising any one of the disclosed peptide conjugates. In some instances, treating the sample having denatured or damaged collagen with a composition comprising any one of the disclosed peptide conjugates requires the administration of a second peptide conjugate that is different than the peptide conjugate administered prior to the detection step. In some instances, only one peptide conjugate administration is required. For example, the peptide conjugate administered prior to detecting can comprise both a detectable moiety and a therapeutic agent. In some instances, the binding of the peptide conjugate to the damaged or denatured collagen can trigger the therapeutic agent to become active and provide therapeutic effects. In some instances, after detecting the binding of the peptide conjugate to the damaged or denatured collagen, a triggering agent can be administered to the sample that turns on or activates the therapeutic agent.

In some instances, the therapeutic agent can be, but is not limited to, any suitable pharmaceutical or other therapeutic agent, including but not limited to, osteogenic promoters, antimicrobials, anti-inflammatory agents, polypeptides such as recombinant proteins, cytokines or antibodies, small molecule chemicals or any combination thereof. In some instances, a therapeutic agent can be a cancer drug, arthritis drug or osteoporosis drug. Therapeutic agents can be capable of promoting bone growth, decreasing inflammation, promoting collagen stability. The therapeutic agent can include, but is not limited to, bone morphogenic protein (BMP), G-CSF, FGF, BMP-2, BMP-3, FGF-2, FGF-4, anti-sclerostin antibody, growth hormone, IGF-1, VEGF, TGF-.beta., KGF, FGF-10, TGF-.alpha., TGF-.beta.1, TGF-.beta. receptor, CT, GH, GM-CSF, EGF, PDGF, celiprolol, activins and connective tissue growth factors. In some instances, a therapeutic agent can be an antibody such as, but not limited to, Avastin, Eylea, Humira, ReoPro, Campath, tocilizumab, Ilaris, Removab, Cimzia, Erbitux, Zenapax, Prolia, Raptiva, Rexomun, Abegrin, HuZAF, Simponi, Igovomab, IMAB362, Imciromab, Remicade, Yervoy, Tysabri, Theracim, OvaRex, Vectibix, Theragyn, Omnitarg, Cyramza, Lucentis, Antova, Actemra, Herceptin, Ektomab, Stelara, HumaSPECT, HuMax-EGFr, HuMax-CD4. A therapeutic agent can target tumors, arthritis, osteoporosis, MMP inhibitors, cathepsin inhibitors, interleukin inhibitors, TRAIL inhibitors, VEGF inhibitors, or CD binding agents.

G. Administration

In the methods described herein, administration or delivery of the peptide conjugates or compositions to cells can be via a variety of mechanisms.

In some instances, the disclosed peptide conjugates and compositions can be administered in a number of ways depending on whether local or systemic treatment is desired, and on the area to be treated.

Preparations of parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for optical administration can include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids, or binders may be desirable. Some of the compositions can be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mon-, di-, trialkyl and aryl amines and substituted ethanolamines.

H. Kits

The compositions and materials described above as well as other materials can be packaged together in any suitable combination as a kit useful for performing, or aiding in the performance of, the disclosed method. It is useful if the kit components in a given kit are designed and adapted for use together in the disclosed method. For example disclosed are kits for making peptide conjugates comprising dimeric collagen hybridizing peptides.

Disclosed are kits comprising an active agent; a spacer moiety; and a dimeric collagen hybridizing peptide comprising a first and second collagen hybridizing peptide; a linker; and a branch point, wherein the first and second collagen hybridizing peptides comprise the sequence of at least (GXY)n (SEQ ID NOs:1-10), wherein G is glycine, wherein X and Y are any amino acid, and wherein n is any number between 3 and 12.

Also disclosed are kits comprising an active agent; a first and a second collagen hybridizing peptide; a linker; and a branching moiety, wherein the first and second collagen hybridizing peptides comprise the sequence of at least (GXY)n (SEQ ID NOs:1-10), wherein G is glycine, wherein X and Y are any amino acid, and wherein n is any number between 3 and 12.

The disclosed kits can also include buffers, reagents, and instructions for how to make the peptide conjugates.

EXAMPLES

A. Example 1

The ability of collagen hybridizing peptides (CHPs, molecular weight 2-3 kDa), formally known as collagen mimetic peptides (CMP), has been shown to to bind specifically to areas of collagen degradation through triple helical hybridization. The CHP is a short peptide which contains repeating motifs of glycine, proline, and hydroxyproline (G-P-O, where O=Hydroxyproline). It has a high propensity to fold into a triple helix at temperatures below its triple helix melting temperature (Tm) and has been shown to bind to denatured collagens I, II, and IV when the peptide is presented to denatured collagen in its single stranded form (not triple helix form).

CHPs bind to collagen strands through triple helical hybridization which involves participation of individual CHP strands. Therefore, CHPs which are in triple helical form cannot bind to denatured collagen and need to be separated (or melted) into individual strands before application to collagen. The easiest way to produce single strand CHP for collagen binding is by heating the peptide above its Tm. However, hot CHP solutions can damage natural tissues, and are therefore not compatible with applications for in vivo and ex vivo collagen binding experiments. A CHP which can be used without heating is greatly desired for translation to practical biomedical uses such as disease imaging and delivery of drug molecules. Such CHP would also allow conjugation of heat- or light-sensitive active agents to CHP.

A new CHP design which has fast folding kinetics even at low concentrations could allow fast and easy drug delivery in vivo. Folding kinetics of single chain collagens exhibit a large concentration dependence, indicating that triple helical folding occurs by first nucleating three chain ends before propagating to fold into a triple helix. Work by Ackerman et al. has shown a reaction order of 2.8 for single strand collagens, suggesting that the rate-limiting step for folding is the encounter of three chains in solution which is concentration dependent. At low concentrations, CHP folding is very slow, potentially limiting the ability of the peptides to form triple helices in the body. This could be one of the major limitations of therapeutic/diagnostic delivery of conventional CHP in vivo.

In this example, the design and synthesis of a dimeric CHP which can be used without heating and has significantly higher folding kinetics when compared to monomeric CHPs is investigated. The dimeric CHP has the two traditional CHPs linked at their C terminus via lysine residue. Dimeric CHP should have an increased ability to bind to collagen strands at low concentrations since only one dimeric molecules need to assemble with collagen strand. This can result in faster folding and the potential to combine with drugs which have high toxicity, as a much lower dosage can be required for similar binding in vivo.

The refolding rate of the dimer in comparison to the previously reported CHPs is investigated, as well as the temperature at which the CHP initiates refolding. The results indicate that the dimeric CHP not only folds faster, but can bind to denatured collagen (porcine gelatin) at a high level without preheating.

1. Structure

The structure of a dimeric CHP can contain four separate components. The first is the branch point, which allows the creation of a dimeric molecule. The branch point defines the linkage of the two arms of the dimeric CHP together. In previous tests, this has been composed of a lysine branch, which allows both arms of the dimeric CHP to be grown simultaneously during solid phase peptide synthesis (SPPS) through coupling to the two amines on the Lys residue. The second component is a flexible linker. This linker can be added for conformational flexibility to the dimeric CHP and allows sterically un-inhibited folding of the triple helix. Selection of a specific linker is not critical, though flexibility can be important. A triple-glycine linker has been used in previous tests, though 6-aminohexanoic acid or a short PEG linker can also be used. The third component is the triple-helix forming region. This region can be composed of repeating segments of Gly-X-Y (wherein X and Y can be any amino acid), which have been shown to form triple helices. This segment can have Gly at every third position. In some instances, a Gly can be required at every third position. X is commonly Pro, but may also be Glu, Asp, among others. Y can be Pro, modified Pro (Hyp, FluoroPro), Lys, or Arg. Any single CHP can be composed of various types of Gly-X-Y repeats. Finally, the fourth component, functional groups (or active agents) can be attached to the end of the peptide (either one or both ends). The functional groups can be imaging moieties (e.g. fluorescent or radioactive probe) or therapeutic molecules and provide functionality to the CHP.

In some instances, in the Gly-X-Y sequence, a glycine residue can be present at every third position otherwise the triple helix will not form. However, in some cases, a small modification to the glycine can be permitted, as in the case of Aza-Glycine, which is expected to form stable triple-helices. The other two positions, X and Y, are able to accommodate virtually any amino acid, although some stabilize the triple helix more than others. Most commonly, proline (P) occupies the X position and hydroxyproline (O) in the Y position. In some instances, the G-P-O sequence forms the most stable triple helix using naturally occurring amino acids. However, modifications to the Y position hydroxyproline are common. Incorporation of unnatural amino acids can often increase the stability of the triple helix, particularly with proline derivatives such as 4-fluoroproline and 4-azidoproline. Proline in the Y position also forms a stable triple helix, though structures formed are not as robust as those made from hydroxyproline. Although these are common amino acids to occupy the X and Y positions, almost any amino acid can be incorporated and still result in a triple helix as long as there is enough Pro and Hyp occupying the X and Y positions. One exception is that charged residues can stabilize the triple helix without the incorporation of Pro or Hyp. In this case, the X and Y positions need to be oppositely charged. X needs to be Asp or Glu and Y needs to be Lys or Arg.

2. Synthesis of Peptides

In this study, peptides were synthesized using standard solid phase peptide synthesis (SPPS) on TentaGel-RAM resin (0.18 or 0.2 mmol/mg loading) using Fmoc-protected amino acids and HBTU chemistry (4 eq amino acid, 4 eq HBTU, 4 eq Cl-HoBT, 8 eq DIEA, 1 hour), unless otherwise stated. Dimeric CHPs were synthesized using Fmoc-Lys (Fmoc)-OH as the branch point, and dimeric CHP was produced by simultaneously growing the chain from both free amines.

Briefly, resin was swelled in DMF for 45 min, deprotected with 20% piperidine in DMF (2×, 15 min), and washed 4× with DMF to prepare resin for amino acid coupling. Amino acids were coupled onto the resin by mixing Fmoc-protected amino acids (4 eq), with HBTU (4 eq), and Cl-HOBt (4eq) was dissolved in DMF and added to the resin. DIEA (6 eq) was then added and the reaction was mixed for 1 h. After coupling, excess reagent was removed with DMF, then the Fmoc protecting group was removed with 20% piperidine in DMF (2×, 15 min), and washed 4× with DMF. The coupling procedure was repeated for each amino acid.

Fluorescent label was conjugated using 6 molar equivalents of CF activated by PyAOP for at least 24 h. Full length peptides were removed from solid support using standard cleavage cocktail of TFA/TIS/H2O (95:2.5:2.5) for 2 h, and cleaved peptides were purified on reverse phase HPLC on a semipreparative Vydac C18 column using a linear gradient of water (0.1% TFA) and acetonitrile (0.1% TFA), 1%/min, 5 ml/min flow rate. Purified peptides were analyzed via matrix assisted laser desorption ionization time-of-flight spectroscopy (MALDI-TOF MS).

3. Results and Discussion

Figure 2:
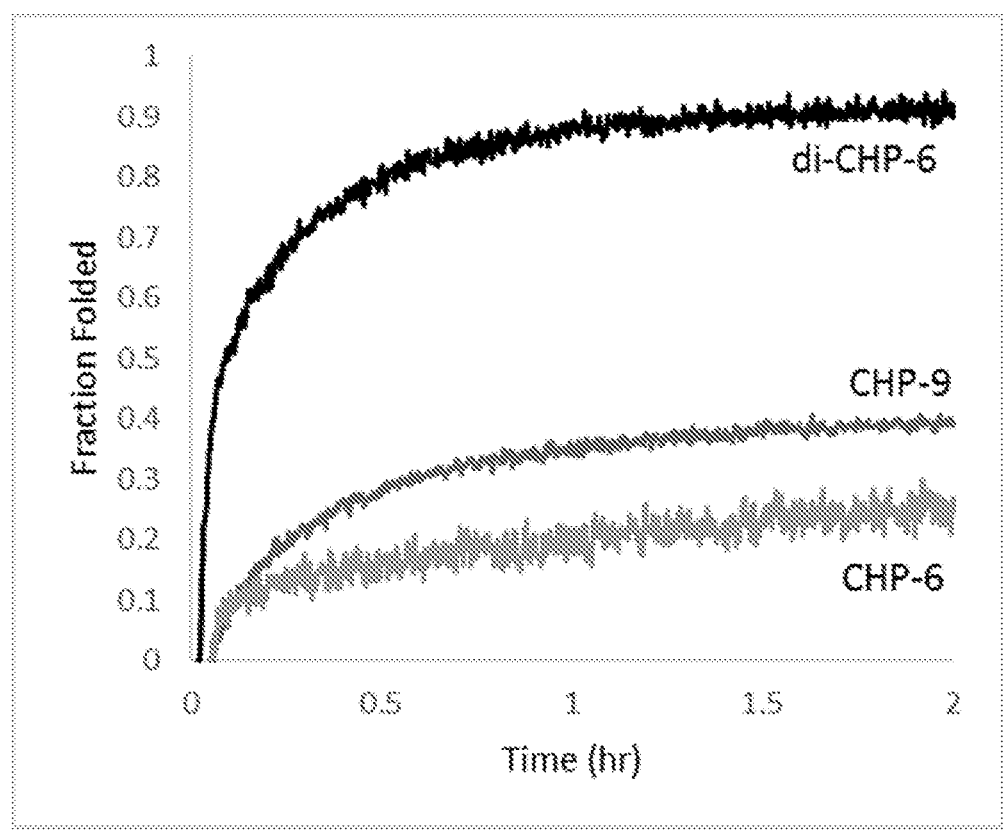
FIG. 2 shows CD data for assemblies of di-CHP-6 (37.5 µM), CHP-9 (60 µM), and CHP-6 (75 µM) monitored at 225 nm over 2 hours. Conversion was assumed to be at 100% after 96 h incubation at 4° C., and max trimer concentration was measured via CD ellipticity at 10° C. Samples were preheated to 80° C. in the sample cuvette for 10 min before being transferred directly to the sample holder held at a constant 10° C. Sample measurement began immediately. Initial time point for analysis was determined by measuring time for a blank (1×PBS) to thermally equilibrate in these conditions.

The dimeric CHP construct folded into a triple helix much faster than the comparable monomeric CHPs, as shown in FIG. 2. Even at relatively high concentrations, di-CHP-6 displayed a faster refolding rate than CHP-6, which did not reach its half maximal refolding after two hours of incubation at 10° C. However, at the same strand concentration, di-CHP-6 almost completely refolded in two hours. This difference was still evident when compared to CHP-9, which refolds faster than CHP-6.

TABLE 1

Sequences and melting points for various novel dimeric CHPs and comparable monomeric CHPs

| CHP | Sequence | $T_m$ (° C.) |
| --- | --- | --- |
| di-CHP-9 | [(GPO)$_9$G$_3$]$_2$KG | 69 (SEQ ID NO: 55) |
| ICHP-9 | (GPO)$_9$ | 68 (SEQ ID NO: 56) |
| di-CF-CHP-9 | [CF-Ahx-(GPO)$_9$G$_3$]$_2$KG | 73 (SEQ ID NO: 55 with label) |
| CF-CHP-9 | CF-G$_3$-(GPO)$_9$ | 69 (SEQ ID NO: 57) |
| di-CHP-6 | [(GPO)$_6$G$_3$]$_2$KG | 38 (SEQ ID NO: 58) |
| CHP-6 | (GPO)$_6$ | 37 (SEQ ID NO: 59) |
| di-CF-CHP-6 | [CF-G$_3$(GPO)$_6$G$_3$]$_2$KG | 50 (SEQ ID NO: 63) |
| CF-CHP-6 | CF-G$_3$-(GPO)$_6$ | 37 (SEQ ID NO: 60) |

Figures 3A, 3B:
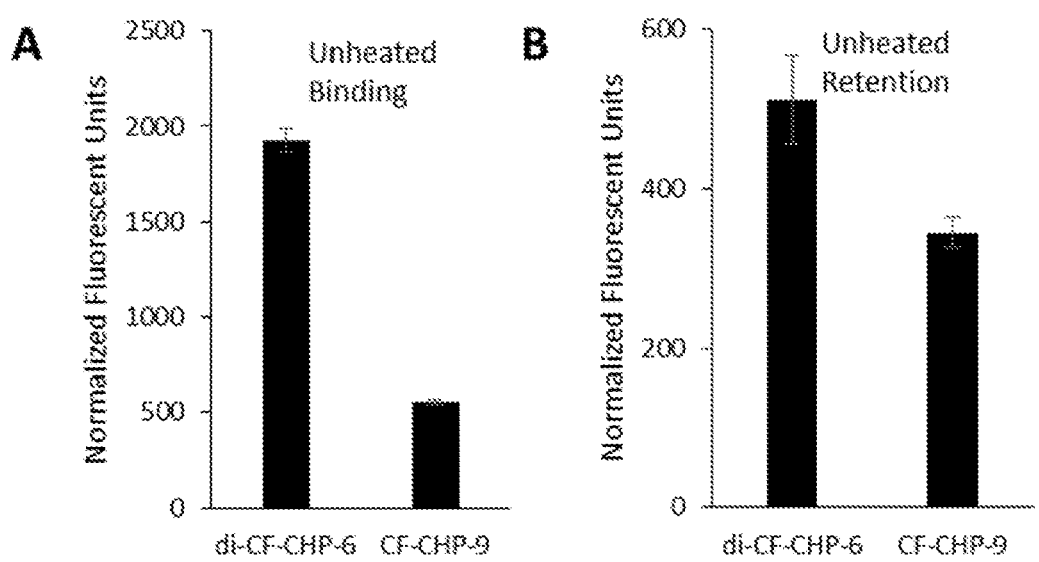
FIGS. 3A and 3B show the affinity of CHPs to gelatin films as monitored by fluorescence of conjugated CF fluorophore (492 ex, 533 em). (A) Fluorescence of CHPs bound to crosslinked gelatin after incubation at 37° C. overnight with no workup. (B) Fluorescence of CHPs remaining in crosslinked gelatin after incubation at 37° C. overnight without preheating, followed by washing with 1×PBS at 37° C. (20 h).

Dimeric CHPs were assessed for their ability to bind to collagen strands in crosslinked gelatin films. CHP solutions (20 µM in PBS) were added directly to the crosslinked gelatin films. For heated experiments, CHPs were preheated to 80° C. for 10 minutes before addition. Peptides were allowed to fully equilibrate with the gel at 37° C. overnight before being exposed to repeated washes (4×, PBS) at 37° C. to fully remove any non-specifically bound peptide and to determine binding level at body temperature. To measure retention, peptides were bound as previously described, but were subsequently washed with PBS 37° C. (5× 1 h, 1× 12 h) to measure retention within the gelatin films. As shown in FIG. 3, significant amount of dimeric CHPs were able to bind to crosslinked gelatin without heating. This level of binding is almost 4 times higher than previously reported for the comparable length CHPs. Additionally, after a period of 20 hours, higher level of the dimeric CHP remained in the gelatin compared to the monomeric CHP. This demonstrates the ability of dimeric CHPs to remain bound to gelatin substrates for long periods of time even at physiologic conditions, indicating their potential use in vivo.

TABLE 2

Sequences and melting points for monomeric and dimeric CHPs with varying GPO repeat units

| CHP | Sequence | $T_m$ (° C.) |
| --- | --- | --- |
| 9 | (GPO)$_9$ | 68 (SEQ ID NO: 56) |
| 9d | [(GPO)$_9$G$_3$]$_2$KG | 69 (SEQ ID NO: 55) |
| CF-9 | CF-G$_3$-(GPO$_9$) | 69 (SEQ ID NO: 57) |
| CF-9d | [(CF-Ahx-GPO)$_9$G$_3$]$_2$KG | 73 (SEQ ID NO: 55 w/ label) |
| b-9 | (GPO)$_9$-G$_3$K$^{Biotin}$ | 68 (SEQ ID NO: 61) |
| b-9d | [(GPO)$_9$G$_3$]$_2$KG$_3$K$^{Biotin}$ | 68 (SEQ ID NO: 62) |
| 9r | (PGOGPGPOPOGOGPOPGOOPGGOOPPG-G$_3$)$_2$KG$_3$K$^{CF}$ | N/A (SEQ ID NO: 72) |
| 6 | (GPO)$_6$ | 37 (SEQ ID NO: 59) |
| 6d | [(GPO)$_6$G$_3$]$_2$KG | 38 (SEQ ID NO: 58) |
| CF-6 | CF-G$_3$-(GPO$_6$) | 37 (SEQ ID NO: 60) |
| CF-6d | [(CF-G$_3$GPO)$_6$G$_3$]$_2$KG | 50 (SEQ ID NO: 63) |
| b-6 | (GPO)$_6$-G$_3$K$^{Biotin}$ | 36 (SEQ ID NO: 64) |
| b-6d | [(GPO)$_6$G$_3$]$_2$KG$_3$K$^{Biotin}$ | 37 (SEQ ID NO: 65) |
| 6r | (PGOPPOGGPOOGOGOPGP-G$_3$)$_2$KG$_3$K$^{CF}$ | N/A (SEQ ID NO: 66) |
| 5 | (GPO)$_5$ | 27 (SEQ ID NO: 67) |
| 5d | [(GPO)$_5$G$_3$]$_2$KG | 27 (SEQ ID NO: 68) |
| CF-5 | CF-G$_3$-(GPO$_5$) | 28 (SEQ ID NO: 69) |
| CF-5d | [(CF-G$_3$GPO)$_5$G$_3$]$_2$KG | 28 (SEQ ID NO: 70) |
| 5r | (PPOGGPOOGOGOPGP-G$_3$)$_2$KG$_3$K$^{CF}$ | N/A (SEQ ID NO: 71) |

Figures 4A, 4B:
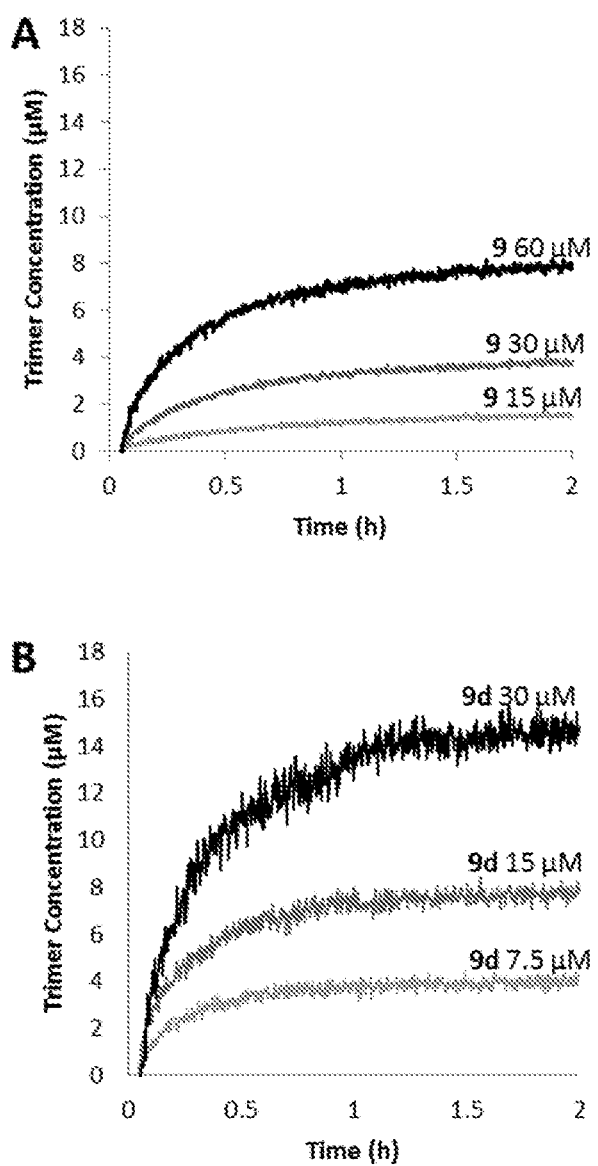
FIGS. 4A, 4B, 4C, and 4D show CD data for assemblies of CHPs 9, 9d, 6, and 6d. For all peptides, conversion was assumed to be at 100% after 96 h incubation at 4° C., and max trimer concentration was measured via CD ellipticity at 10° C. Samples were preheated to 80° C. in the sample cuvette for 10 min before being transferred directly to the sample holder held at a constant 10° C. Sample measurement began immediately. Initial time point for analysis was determined by measuring time for a blank (1×PBS) to thermally equilibrate in these conditions. This was set as the zero point for all peptides, as the large jump in CD due to temperature makes the initial jump irresolvable. (A) Rate of assembly of CHP 9 (60, 30, and 15 µM), over 2 h, monitored at 225 nm. (B) Rate of assembly of CHP 9d (30, 15, and 7.5 µM, corresponding to same CHP strand concentration from panel A), over 2 h, monitored at 225 nm. (C) Rate of assembly of CHP 6 (150 and 75 µM), over 2 h, monitored at 225 nm. (D) Rate of assembly of CHP 6d (75, 37.5, and 15 µM, corresponding to same CHP strand concentration from panel C with an additional lower concentration), over 2 h, monitored at 225 nm.
Figures 4C, 4D:
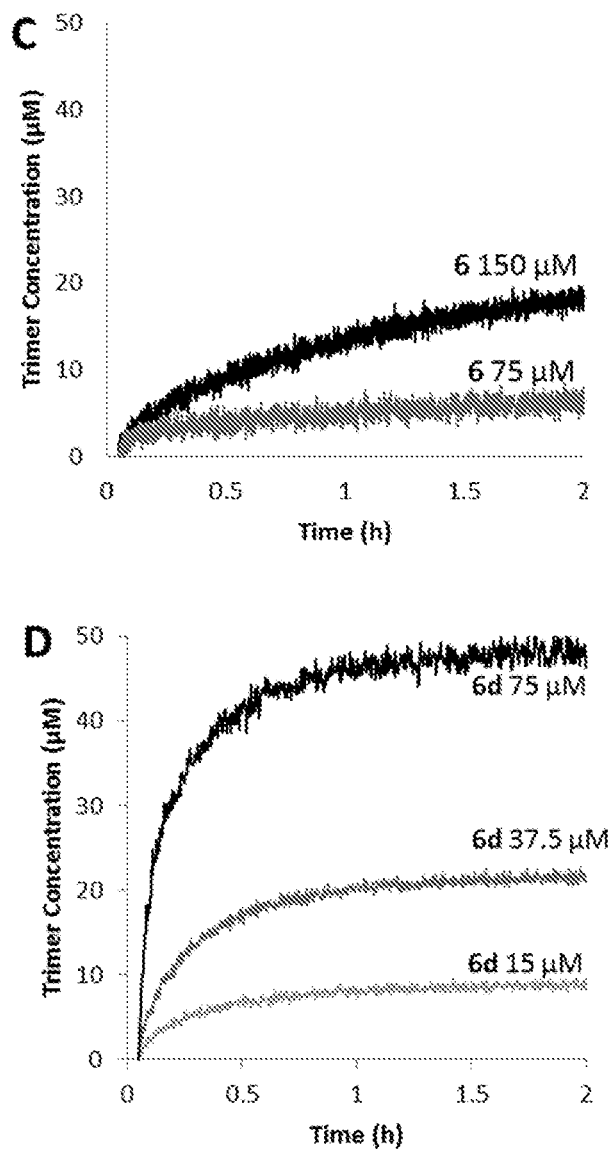

There was a large difference in the refolding rate between the monomeric and dimeric CHPs, which was especially evident with fewer GPO repeats (FIG. 4). Even at relatively high concentrations, the GPO¬6 monomer (6) displayed a slower refolding rate than the GPO¬6 dimer (6d), and did not reach its half maximal refolding after two hours of incubation at 10° C. However, at the same strand concentration, the dimeric GPO6 (6d) almost completely refolded in two hours. This difference was still evident when comparing the GPO9 monomer (9) and dimer (9d), though the GPO9 monomer refolds much more quickly than the GPO6 monomer.

Figures 5A, 5B:
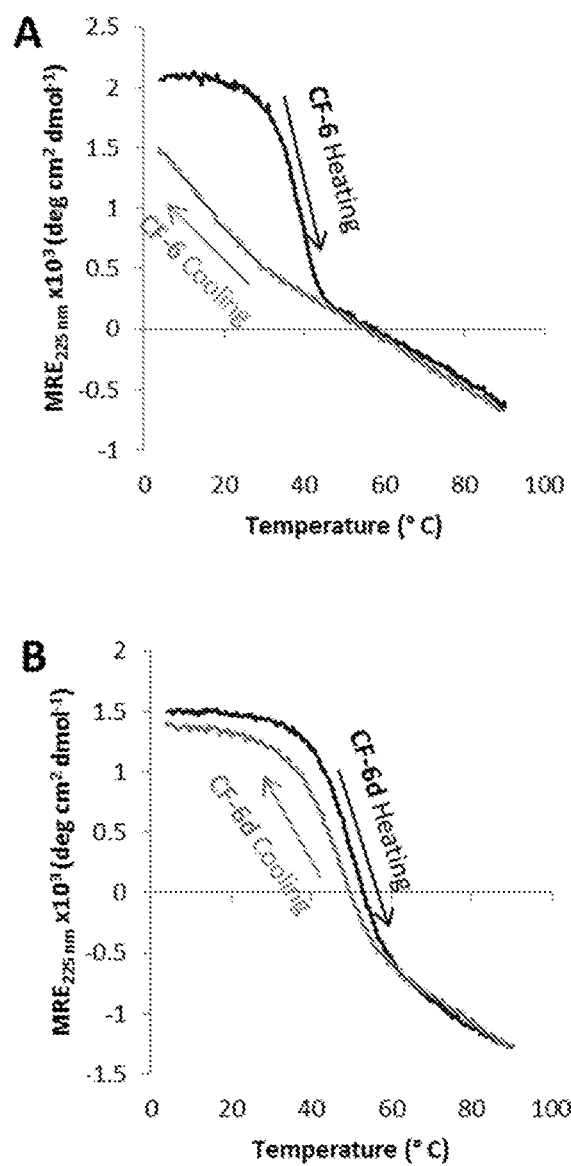
FIGS. 5A, 5B, 5C, and 5D show the thermal denaturation of fully assembled CHPs and subsequent cooling to initial temperature. Samples were heated at 1° C./min from their initial temperature final temperature of 90° C. Sample was then cooled at 1° C./min to the starting temperature. (A) Thermal denaturation and partial reassembly of CHP CF-6d (150 µM) monitored at 225 nm. Sample was measured from 4° C. to 90° C. (B) Thermal denaturation and partial reassembly of CHP CF-6 (75 µM, corresponding to 150 µM strand concentration) monitored at 225 nm. Sample was measured from 4° C. to 90° C. (C) Thermal denaturation and partial reassembly of CHP CF-9 (150 µM) monitored at 225 nm. Sample was measured from 10° C. to 90° C. (D) Thermal denaturation and partial reassembly of CHP CF-9d (75 µM, corresponding to 150 µM strand concentration) monitored at 225 nm. Sample was measured from 10° C. to 90° C.
Figures 5C, 5D:
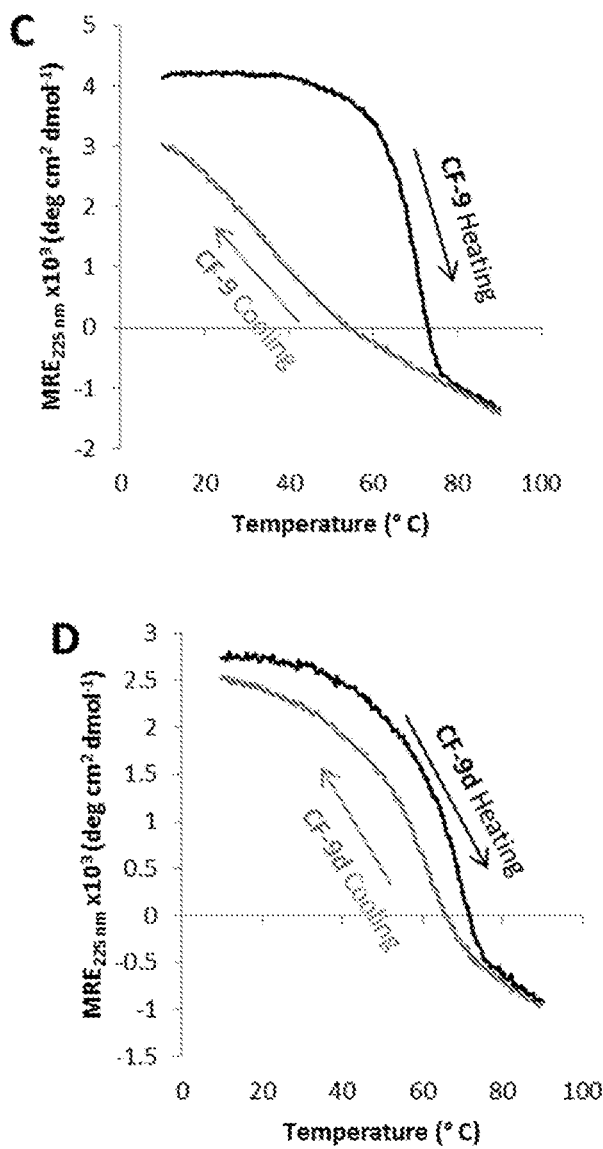

The dimeric CHPs can also form their triple helices much more readily during slow cooling when compared to their monomeric counterparts. After thermal denaturation and heating to 90° C., the peptides were exposed to a decreasing thermal gradient from 90 to 4° C. (1° C./min) during which the ellipticity at 225 nm was monitored. During these cooling gradients, the dimeric CHPs began refolding at a higher temperature than the monomers with the same number of repeat units. No significant refolding was observed until approximately 10 and 15° C. below the reported Tm in the case of the GPO6 monomer and GPO9 monomer, respectively. However, a significant refolding was observed immediately in the case of all dimeric CHPs tested, and an almost complete return to preheated ellipticity by the end of the cooling gradient, as shown in FIG. 5.

Figures 6A, 6B:
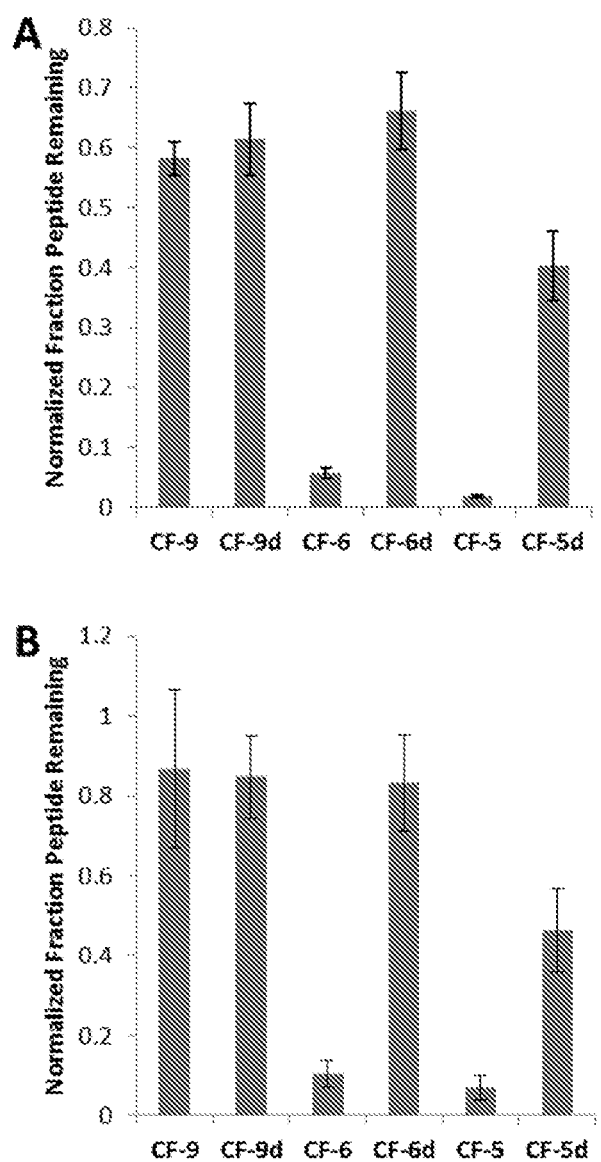
FIGS. 6A, 6B, 6C, and 6D show the affinity of CHPs to gelatin films as monitored by fluorescence of conjugated CF fluorophore (492 ex, 533 em). (A) Fraction of peptide remaining in a crosslinked gelatin film after 17 h at 25° C. (10 total washes). Values are normalized to fluorescence remaining in wells after 6 washes at 4° C. (>95% removal of CHPs 9r, 6r, and 5r). All washes performed in 1×PBS. (B) CHPs (15 µM) premixed into 10% porcine gelatin and preheated to 80° C. (10 min) before being added to a 96 well plate. Excess CHP-gelatin mixture was removed, then the premix was incubated at 4° C. for 2 hours. Wells were washed at 4° C., 5 times (>95% removal of CHPs 9r, 6r, and 5r). Wells were then washed for 2 hours (6 washes total) at 25° C. to monitor CHP remaining in the well. (C) Fluorescence of CHPs remaining in crosslinked gelatin after incubation at 37° C. overnight without preheating, followed by washing with 1×PBS at 37° C. (20 h). (D) Fluorescence of CHPs remaining in crosslinked gelatin after incubation at 37° C. overnight (80° C. preheating, 10 min), followed by washing with 1×PBS at 37° C. (20 h).

Binding to Gelatin films. Peptide solutions (20 µM in PBS) were preheated to 80° C. for 10 minutes before being added directly to the crosslinked gelatin films. Peptides were allowed to fully equilibrate with the gel at 4° C. overnight before being exposed to repeated washes (4×30 min) at 4° to fully remove any non-specifically bound peptide. Gelatin wells were then washed at r.t. with PBS (5× 1 h, 1× 12 h) to measure retention within the gelatin films. In each case, the dimeric CHPs had higher retention than that of the comparable monomer. Monomeric GPO5 (CF-5) and GPO6 (CF-6) were almost entirely washed out of the gelatin films, indicating these compounds do not have high affinity to gelatin at this temperature. Even with a much lower melting point, the GPO5 dimer (CF-5d) displayed a higher affinity to the gelatin films than CF-6. Similarly, the GPO6 dimer (CF-6d) demonstrated a comparable affinity to that of the GPO9 monomer (CF-9) and GPO9 dimer (CF-9d), all of which had similar retention in the gelatin films, as shown in FIG. 6A. To eliminate the possibility of these peptides merely becoming physically entrapped within the gelatin after forming triple helix or forming triple helix before binding, binding affinity was verified by producing a premix of the CHPs and Gelatin to eliminated diffusion-limited binding before washing the wells in a similar manner. As show in FIG. 6B, all peptides tested had slightly higher retention in the gelatin films when compared to FIG. 6A, indicating that the CHPs may be binding to a higher fraction of gelatin vs self-assembly, as was expected.

Figures 6C, 6D:
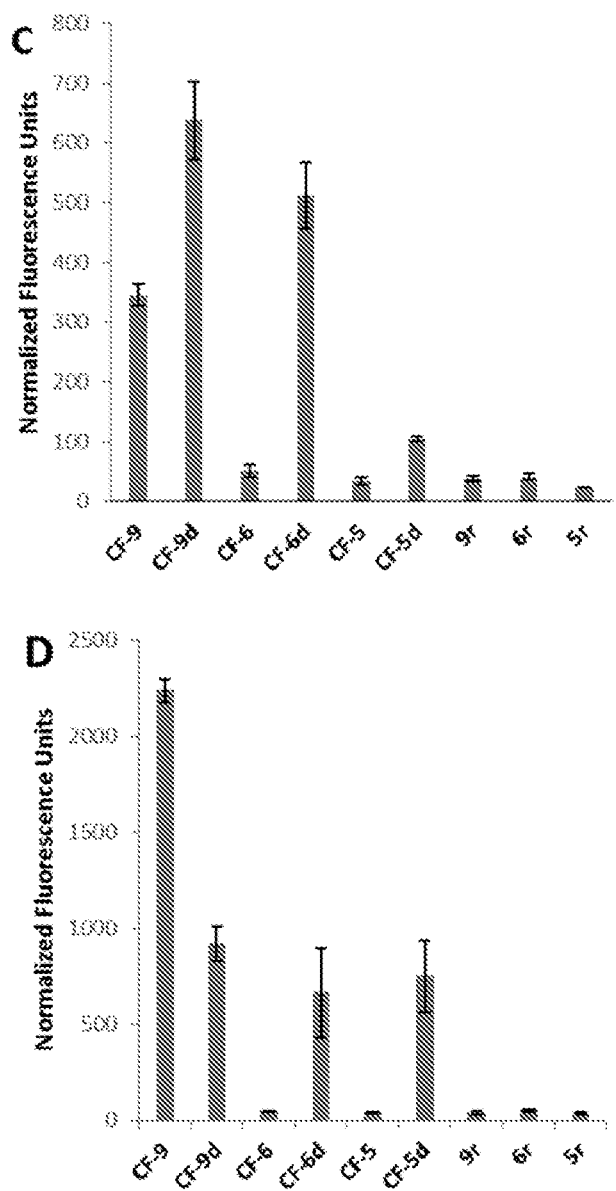

A major limitation of the use of CHP in vivo, is the requirement of the triple helix to be fully disassembled before being injected. Since the dimeric CHPs exhibited increased affinity to gelatin with a significantly lower melting point, it is possible the dimeric CHPs can demonstrate significant binding to gelatin films without prior preheating. The peptides' ability to bind to gelatin films at physiologic temperature was determined with and without any preheating in a similar manner to the previous binding assay, as shown in FIG. 6C, 6D. For this test, peptide solutions were allowed to warm to room temperature before being added (50 µL, 20 µM) to previously prepared crosslinked gelatin films. Solutions were then incubated at 37° C. overnight before removing the solution. Wells were washed at 37° C. with PBS (20 h) to determine binding. Preheated samples were prepared and incubated in the same way, but with preheating (80° C., 10 min) before being added to the crosslinked gelatin wells.

All three dimeric CHPs tested were able to bind significantly to the gelatin wells, with the GPO9 and GPO6 dimer demonstrating an ability to bind more significantly than the GPO9 monomer without preheating. This is likely due to the relatively lower melting point of the GPO6 dimer, which can partially unfold at physiologic temperatures and allow binding to the gelatin. Alternatively, the production of a triple helix in the dimeric state can leave an open CHP strand, which is still able to bind to gelatin at these conditions, and is likely the case for the GPO9 dimer's ability to bind without preheating. No monomer was found to bind significantly without preheating. GPO5 and GPO6 monomers do not have a strong enough affinity to the gelatin to bind effectively at physiologic temperature, although 37° C. is enough to dissociate these CHPs, so any peptide bound in this case is quickly eluted. Additionally incubation at 37° C. is not enough to disrupt the GPO9 triple helix, and thus the GPO9 monomer is unable to bind significantly without preheating.

Figures 7A, 7B:
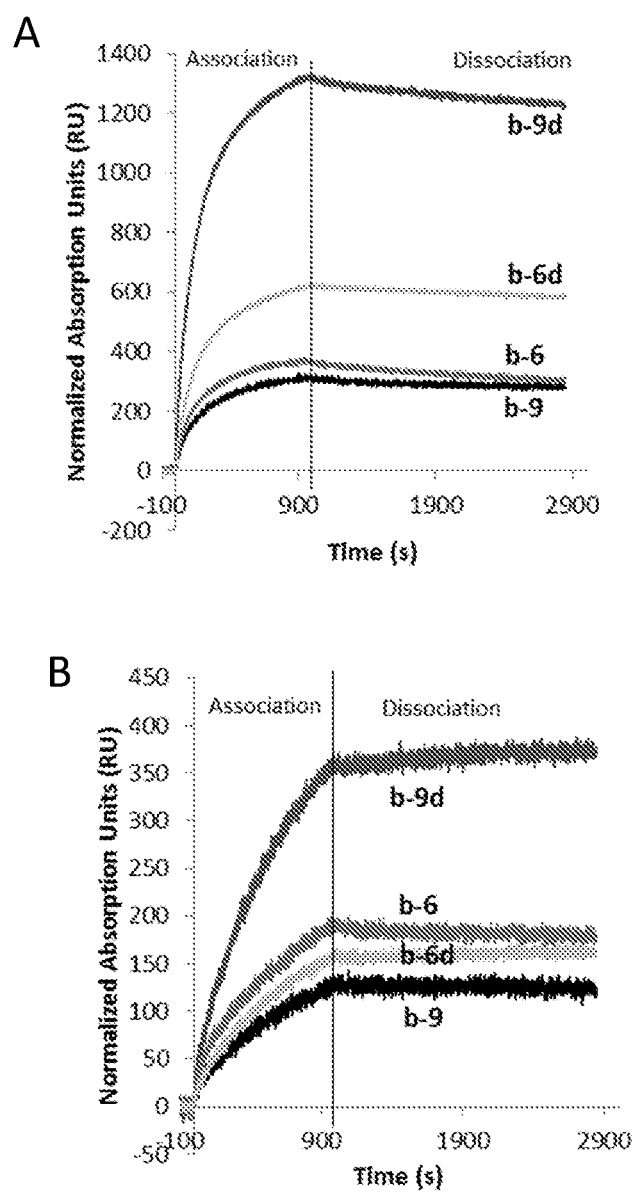
FIGS. 7A and 7B show SPR data for porcine gelatin capture by immobilized CHPs. CHPs b-9, b-9d, b-6, and b-6d were immobilized on neutravidin coated NLC sensor chips (Bio-Rad) at approximately 40% of max loading, then fully blocked with biotin. Gelatin was applied to the sensor surface during the association phase, followed by elution with blank during dissociation phase. Association occurred for 981 s, followed by dissociation for 1800 s. Values were normalized to a 100% biotin lane, and were adjusted to the mass of peptide immobilized in each well. (A) Preheated (80° C., 10 min), quenched (0° C., 30 s) gelatin (25 µg/mL) was applied to the sensor at an ambient temperature of 37° C. (B) Preheated (80° C., 10 min), quenched (0° C., 30 s) gelatin (25 µg/mL) was applied to the sensor at an ambient temperature of 15° C.
Figure 8:
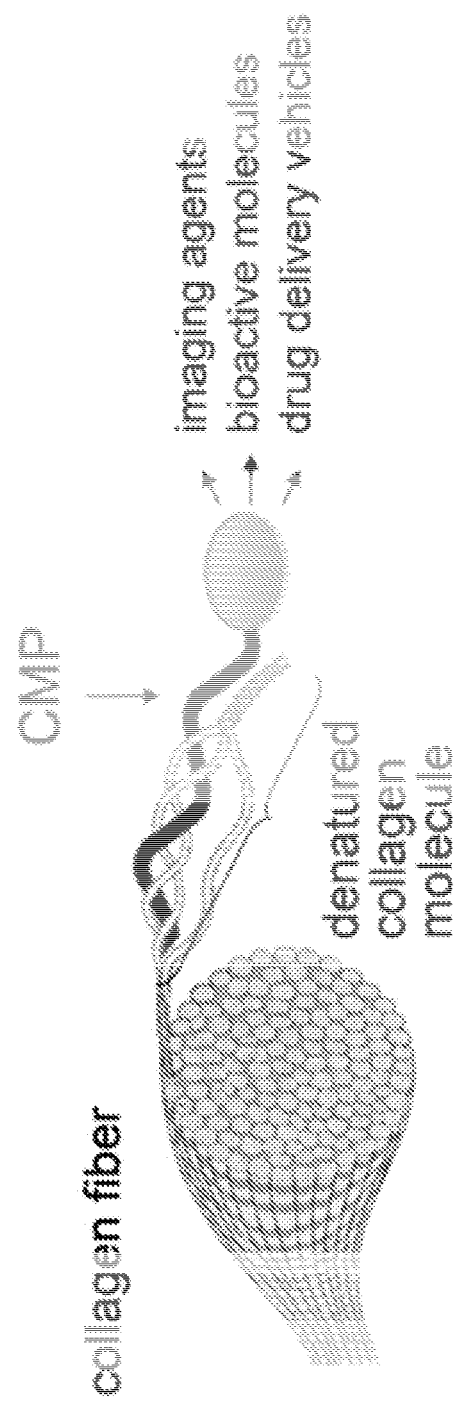
FIG. 8 is a schematic drawing showing the interaction of a collagen hybridizing peptide with a denatured collagen molecule.
Figure 9:
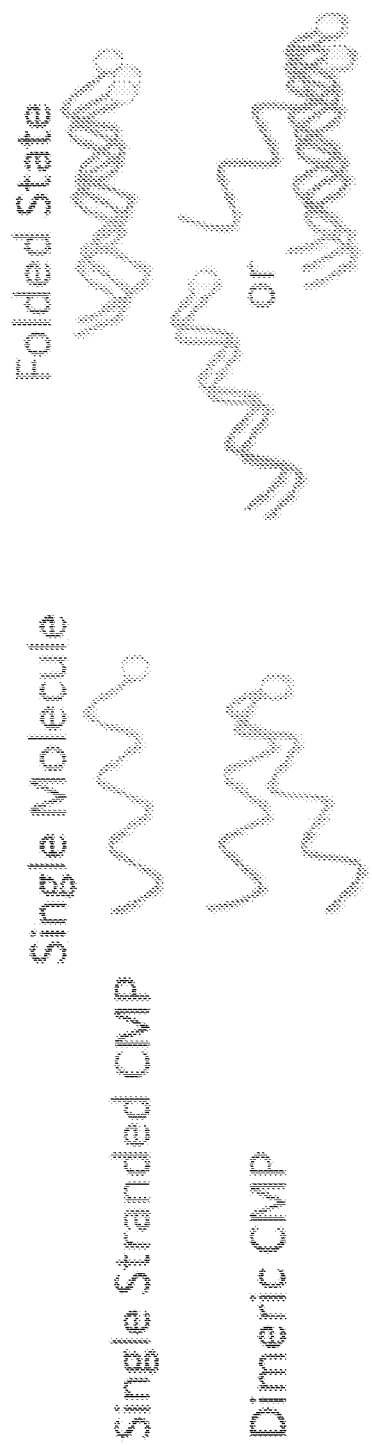
FIG. 9 shows a schematic drawing of the monomers and dimers alone or in their folded state.
Figure 10:
FIG. 10 is a schematic of the synthesis of monomers and dimers of collagen hybridizing peptides. The sequence shown represents SEQ ID NOs: 73-82.
Figure 11A:
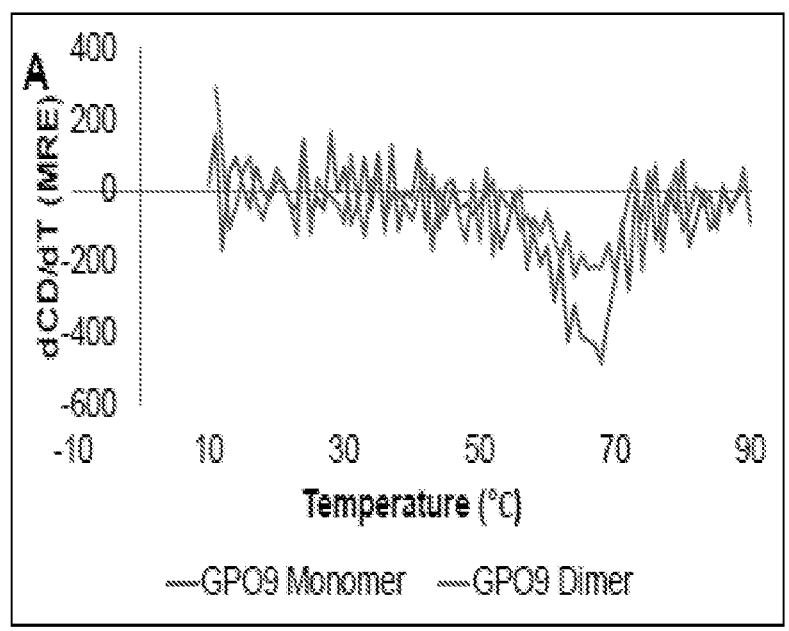
FIGS. 11A and 11B show the First Derivative of mean residue ellipticity (MRE) at 225 nm in CD. Panel A shows the melting points of the GPO9 monomer and dimer. Panel B shows the melting points of GPO6 monomer and dimer. There is no significant change in melting point between the monomeric and dimeric forms of the same peptide.
Figure 11B:
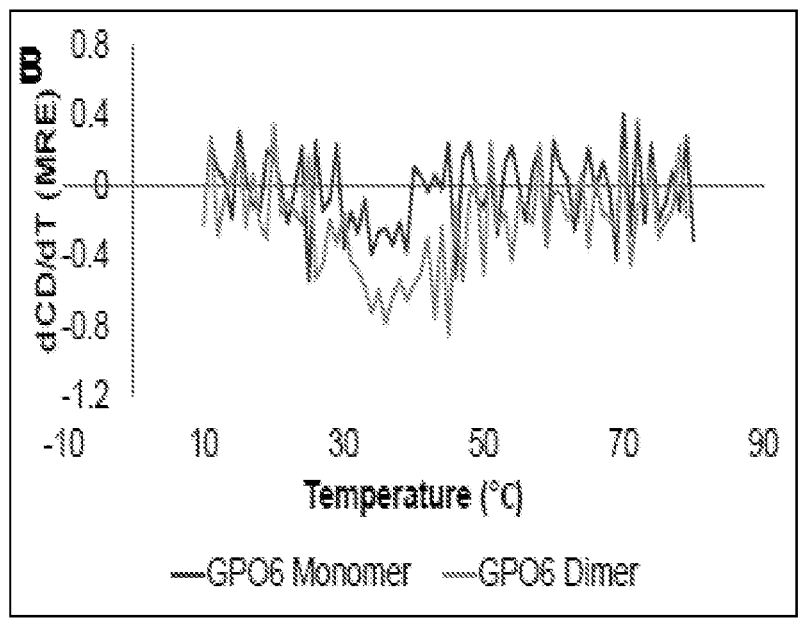
Figure 12A:
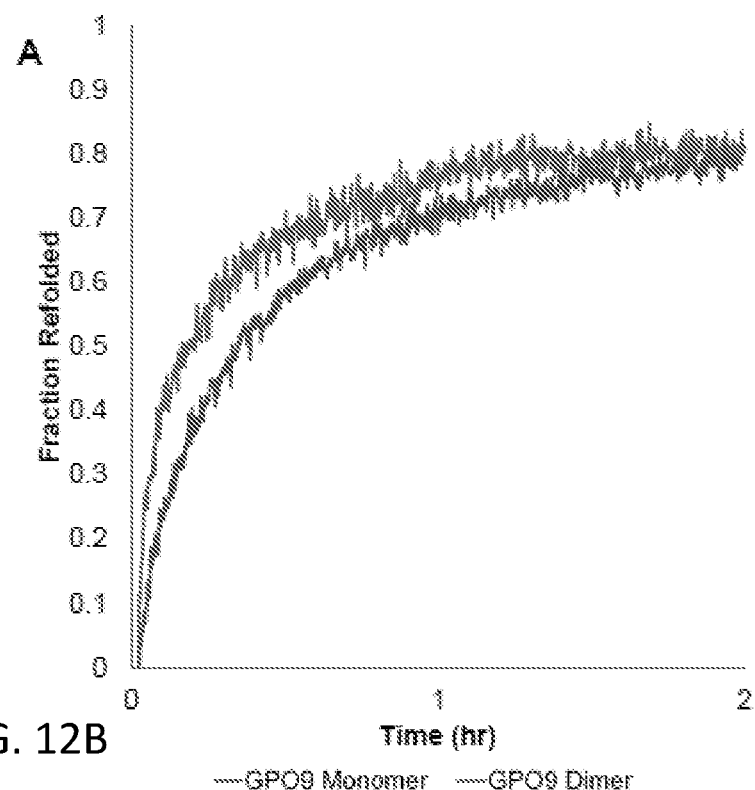
FIGS. 12A and 12B show CD refolding at 10° C. of CMPs monitored at 225 nm. CMPs were heated to 80° C. for 5 minutes before being placed into the CD and initial 2 min of monitored data was removed to eliminate thermal transition. Signal was normalized to that of a fully folded peptide. Panel A shows an approximate two-fold increase in refolding rate of the GPO9 dimer compared to monomeric GPO9. Panel B shows the drastic difference in refolding rate between the GPO6 monomer and dimer.
Figure 12B:
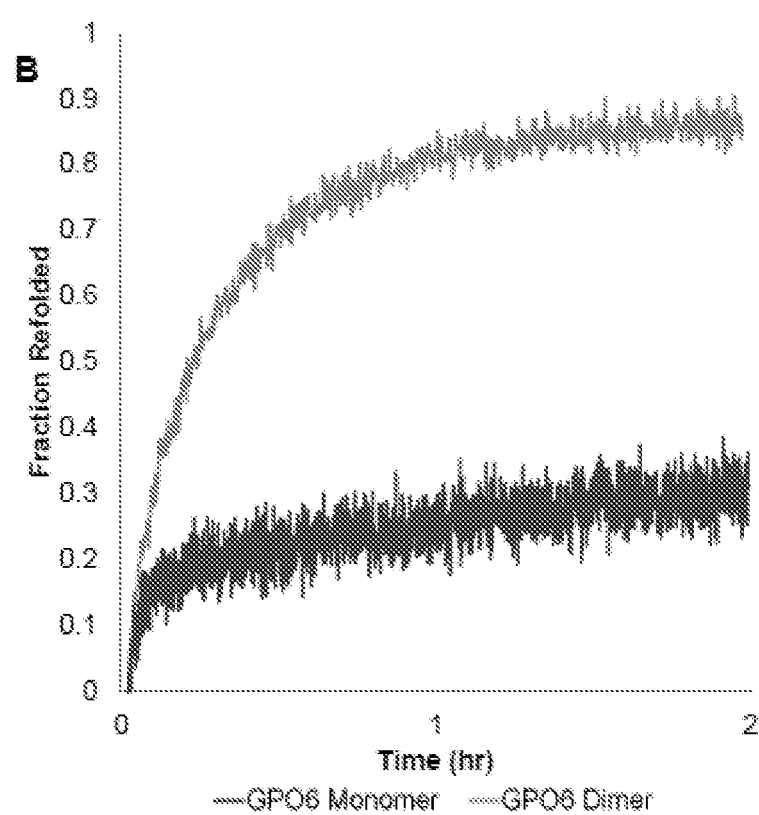
Figure 13:
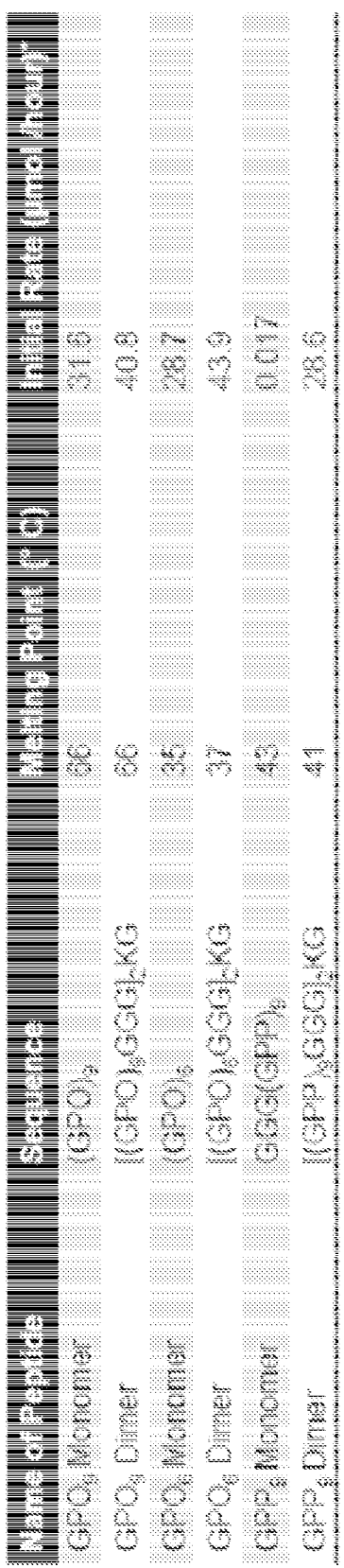
FIG. 13 is a table showing the summary of melting points and initial refolding rates for various monomeric and dimeric CMPs. *Initial rate taken at 30 µM strand concentration (15 µM peptide for dimers). From top to bottom the sequences are SEQ ID NO: 56, SEQ ID NO: 51, SEQ ID NO: 59, SEQ ID NO: 11, SEQ ID NO: 83, and SEQ ID NO: 84.
Figure 14:
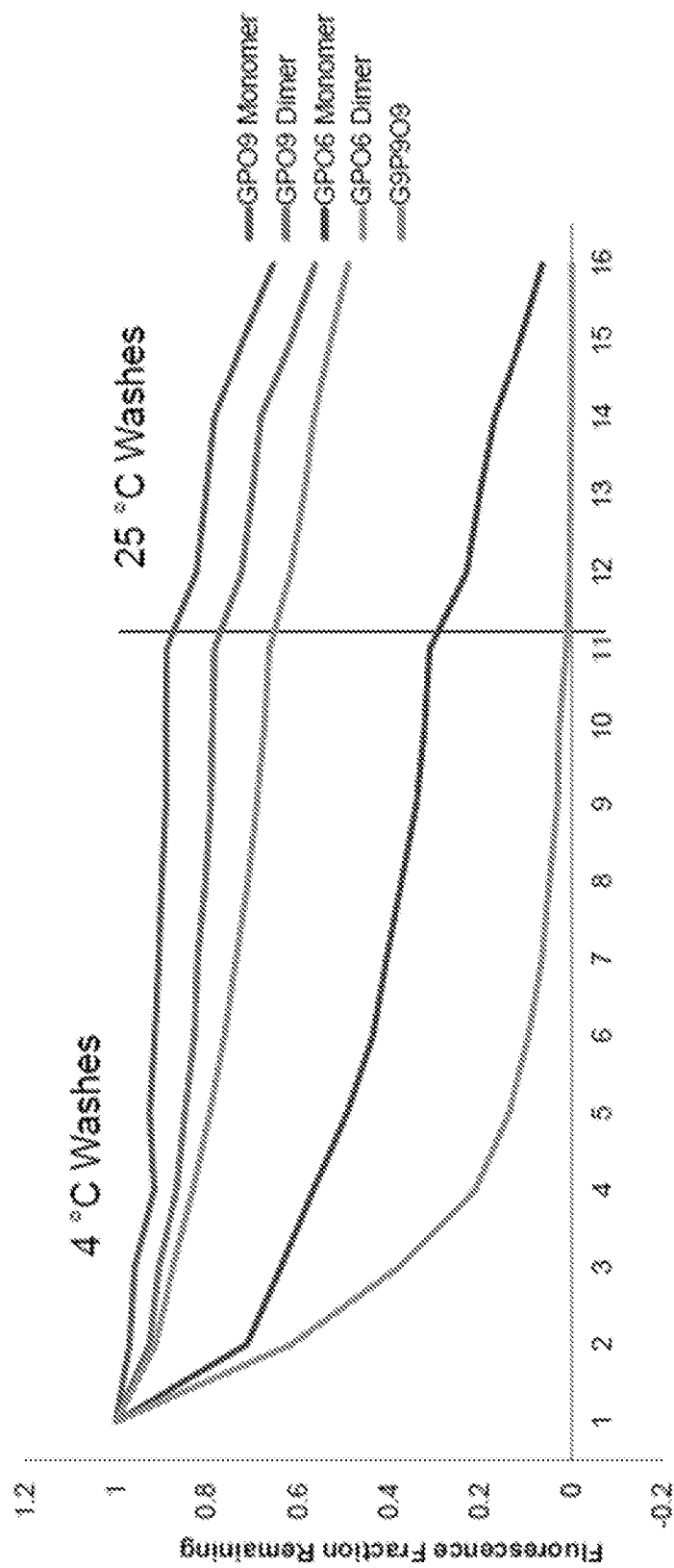
FIG. 14 shows a fraction of initial fluorescent CF-CMPs remaining in thin gelatin film after repeated washes. Fluorescence was monitored at 489 nm excitation, 530 nm emission, with a 515 nm cutoff. Peptides were plated on the films at 50 µM and were allowed to bind to the gelatin overnight. Initial 4° C. washes were repeated until the random, non-triple helix forming CMP (G9O9P9) was fully removed from the wells. Washes were then continued at 25° C. The lines in order from top to bottom are GPO9 monomer, GPO9 dimer, GPO6 monomer, GPO6 dimer, G9P9O9.

Surface Plasmon Resonance (SPR). The SPR curve for all experiments shows a rapid association of gelatin to the peptide during the association phase, and no or very little dissociation of the gelatin during the dissociation phase (FIG. 7). At 15° C., there is virtually no decrease in signal intensity during the dissociation phase, indicating that the gelatin is tightly bound to the peptides, and none is being removed. However, at 37° C., a small signal decrease is observed, indicating that there is a small fraction of the bound peptide which is eluted during the dissociation phase. This effect was observed for all peptides tested. However, there were major differences observed during the association phase. At 37° C., there was a much higher amount of gelatin adsorbed to all the peptides tested on the surface when compared to 15° C. Additionally, at 37° C., both the dimeric GPO6 and GPO9 demonstrated a higher ability to bind gelatin than that of an equivalent number of strands in their monomeric counterparts. Surprisingly, the monomeric GPO6 and GPO9 did not differ greatly in their ability to bind gelatin, indicating that the binding rate is more dependent on the gelatin forming a triple helix than that of the CHP. At 15° C., gelatin adsorbed to the surface at a much slower rate. Since triple helices only form at low temperatures, this result was unexpected, as lower temperature would be expected to drive triple helix formation. However, this lower adsorption rate can be due to a reduced diffusion rate near the surface or a more condensed gelatin structure at this lower temperature. Additionally, at 15° C., the GPO9 dimer maintained its greater ability to bind gelatin, but the GPO6 dimer was only able to bind gelatin at a rate comparable to the monomeric CHPs.

4. Discussion

Dimeric collagen hybridizing peptides were found to refold much more readily than monomeric CHPs which can be due to increased nucleation rate. There is an increase in binding affinity with dimeric CHPs in comparison to monomeric form (higher GPO yields higher stability). There is larger binding without preheating than currently used CHPs. Dimeric collagen hybridizing peptides were also able to bind more gelatin at physiologic temperature than monomers.

B. Example 2

Collagen is an integral component of the extracellular matrix, and a high proportion of collagen is degraded and turned over in the body each day. However, there are many pathological conditions which are characterized by an excess of collagen remodeling. Collagen Hybridizing Peptides (CHPs) are small peptides composed of GXY repeats which are able to selectively hybridize denatured collagen strands in vitro and in vivo, something which is often difficult using conventional approaches. CHP binding has been found to be driven primarily by triple-helical hybridization with denatured collagen strands. As such, CHPs can be used as a targeting moiety nanoparticles, imaging modalities, or other therapeutic agents to areas of denatured collagens in the body. However, current CHPs are limited by their binding affinity and slow folding kinetics, which results in a high proportion of peptide cleared by the body before they are able to bind to the areas of interest.

A potential way to increase the binding kinetics of CHPs is to increase their local concentration. There have been many studies which have produced a template CHP, but these contain all three required strands, and therefore cannot bind denatured collagen. The production of a two-stranded CHP would increase the local strand concentration while still allowing the peptide to bind denatured collagen. Additionally, the binding affinity may increase due to multivalency, as the two strands need not form a single complex, or due to increased hydroxyproline content per helix.

1. Methods

Peptide Synthesis: Peptides used in this study were prepared via solid phase peptide synthesis (SPPS), through standard Fmoc procedures. They were purified by RP-HPLC and verified by MALDI-TOF MS. The dimeric CHPs branch was assembled via a doubly Fmoc protected Lysine, which results in two identical strands during N-terminal extension, suitable for producing a dimeric CHP.

Circular Dichroism: Circular Dichroism (CD) was measured for all peptides at 225 nm. Melting curves were taken on peptides between 10 and 80° C. at a heating rate of 0.5° C./min, with pauses at each 1° C. Refolding experiments were performed after peptide solutions were incubated at 4° C. for at least 12 hours. Concentrations were normalized to strand concentration.

Fluorescence Binding: CHP binding to gelatin was monitored by conjugating a fluorescent Carboxyfluorescein (CF) molecule to the N-terminus of each peptide via standard SPPS. Solutions of the fluorescent peptides were heated to 80° C. for 5 min before injecting 50 µL onto a pre-prepared EDC-crosslinked thin gelatin film in a 96 well plate. Peptides incubated overnight at 4° C., then washed with repeated rounds of 4° C. 1×PBS followed by 25° C. 1×PBS.

The dimeric form of CMP, at both six and nine repeat units did not differ in melting point to that of its respective monomeric form, but dramatically increased the refolding rate in solution. This difference was much more distinct in smaller CMPs.

2. Conclusions

There was a clear increase in binding affinity for the dimeric GPO6 compared to its monomeric form. Binding affinity of the CHPs to gelatin is indirectly measured as the washing steps are predominantly diffusion-mediated. The increase in binding affinity and folding rate allow dimeric CHPs to be used in vivo directly without any previous preparation such as melting or deprotection, as is the case for monomeric CHPs. These dimeric CHPs are easily functionalized with peptides or other molecules and can be used as a stronger targeting modality to denatured collagen than monomeric CHPs.

C. Example 3

A collagen hybridizing peptide (CHP) has been developed which increases the binding rate and affinity to denatured collagen materials, such as gelatin. Collagen is an integral component of the extracellular matrix, and a high proportion of collagen is degraded and turned over in the body each day. However, there are many pathological conditions which are characterized by an excess of collagen remodeling. Collagen Hybridizing Peptides (CHPs) are small peptides composed of GXY repeats which are able to specifically hybridize denatured collagen strands in vitro and in vivo. Differentiating native vs denatured collagens is very difficult using standard methods (antibodies, picrosirius red). CHP binding has been found to be driven by triple-helical hybridization, which occurs only with denatured collagen strands. As such, CHPs have the ability to be used to target nanoparticles, imaging modalities, or other therapeutic agents to areas of denatured collagens in the body. However, current CHPs are limited by their binding affinity and slow folding kinetics, which results in a high proportion of peptide cleared by the body before they are able to bind to the areas of interest.

A two armed (dimeric) CHP has been developed which serves to increase the local concentration of triple-helix forming strands while still allowing the CHP to readily bind to the gelatin. This local concentration increases the folding rate to other triple-helix forming strands. This dimeric CHP has also been shown to increase the binding affinity to gelatins, particularly with shorter CHP dimers. These dimeric CHPs have the ability to bind in the same way as currently utilized CHPs but can do so with significantly faster binding rates without compromising affinity. These features can allow a higher proportion of targeted molecules to successfully bind to the desired collagen substrates.

The new compound is a dimeric CHP with the amino acid sequence: [(GPO)6G3)2KG. It is composed of two identical G-P-O (O=hydroxyproline) strands connected through a single, lysine branch point and can be modified on both ends to contain various imaging or therapeutic modalities. The dimeric CHP can be synthesized entirely on resin using standard solid phase peptide synthesis methods, including modifications to both the N and C terminus.

Figure 15:
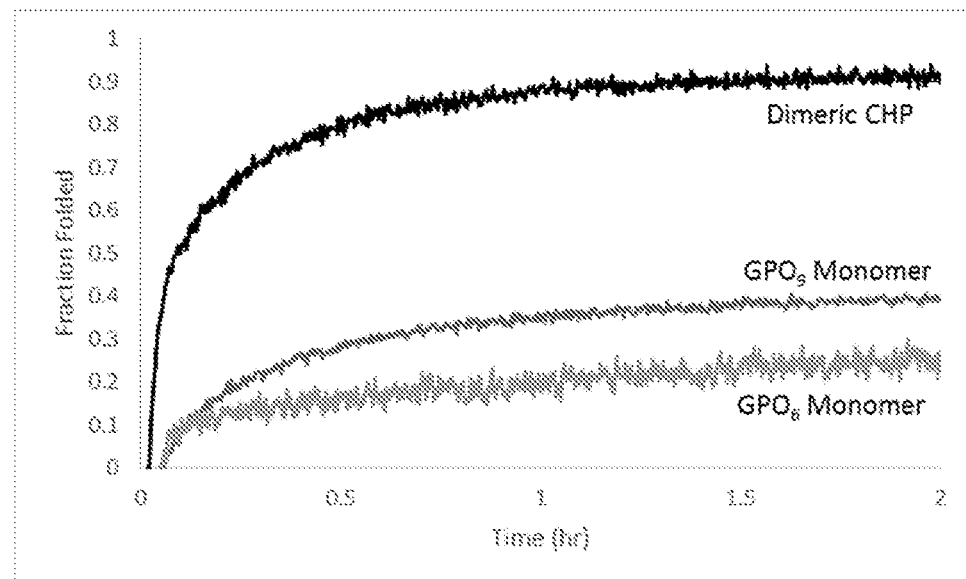
FIG. 15 shows the refolding comparison between dimeric CHP and monomeric. CHPs.

The inclusion of two strands on a single molecule does not have a significant impact on the melting point, with the dimeric CHP having an almost identical melting point (38° C.) as a monomeric CHP with the same number of G-P-O repeats (GPO6, 37° C.). This melting point is much lower than the currently utilized CHPs (GPO9) which have a melting transition at 68° C. Additionally, in spite of the lower melting temperature, the dimeric CHP has a much faster refolding rate than current monomeric CHPs. In CD refolding experiments, dimeric CHP at 37.5 µM was half refolded at 10 minutes, whereas 60 µM GPO9 was 40% folded after 2 hours, and 75 µM GPO6 was 28% folded after 2 hours (FIG. 15). Finally, in gelatin retention studies, dimeric CHP demonstrated a similar affinity to gelatin films as current monomeric CHPs.

Figure 16:
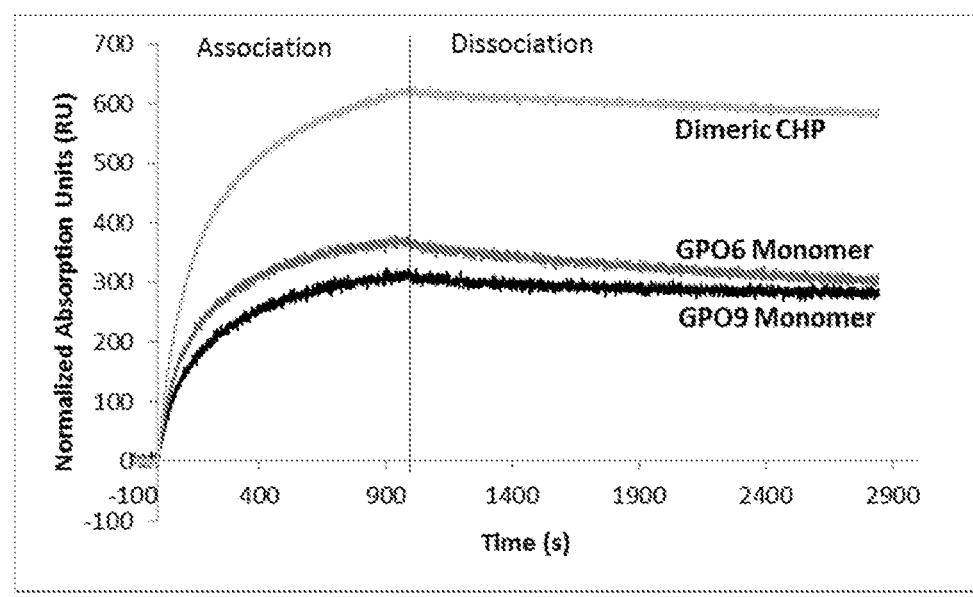
FIG. 16 shows the SPR association and dissociation curves for dimeric CHP vs monomeric CHPs.

Dimeric CHP is able to hybridize effectively with denatured collagens with faster folding kinetics than current, monomeric CHPs. Surface plasmon resonance (SPR) was used to measure the ability of the CHPs to trap denatured collagen from solution. Biotinylated, dimeric CHPs immobilized to the SPR surface were able to capture and retain approximately twice the amount of gelatin vs comparable CHPs in the same conditions (FIG. 16). Additionally, dimeric CHP demonstrated a Kd of 0.621 µM at 25° C. which is almost identical to a biotinylated GPO9 (Kd=0.573 µM, 25° C.) in an ELISA-like assay.

Figure 17:
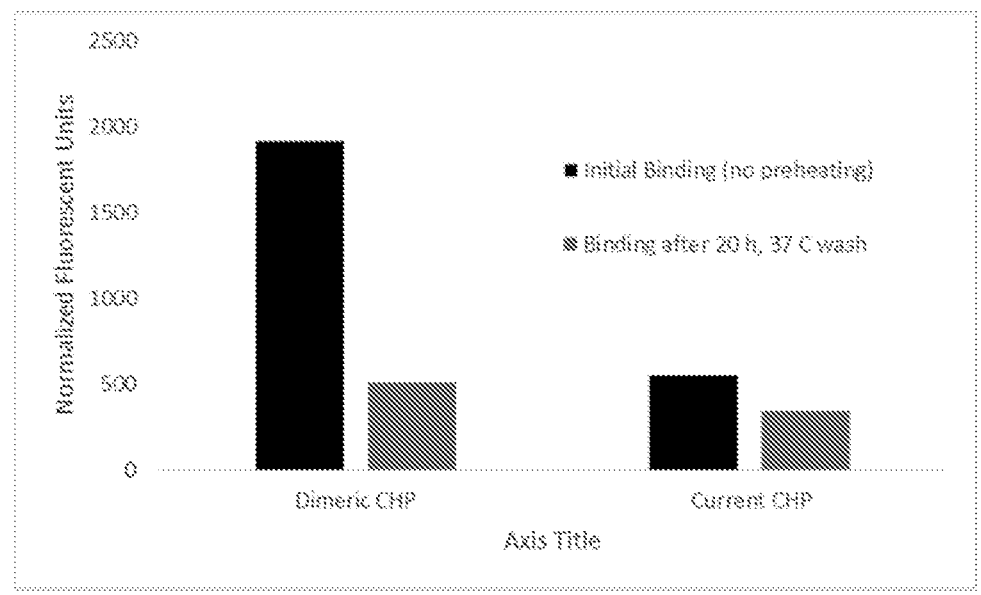
FIG. 17 shows the initial binding, and remaining fluorescence in Gelatin retention assay using non-preheated peptides.

In retention studies using crosslinked gelatin films, slightly more fluorescently labelled dimeric CHP was shown to remain bound to the gelatin substrate than the currently utilized CHP (66% retention dimeric CHP vs 58% CHP). Additionally, the fluorescently labelled, dimeric CHP demonstrated 350% higher initial binding to the gelatin substrate and 50% more peptide remaining after 20 hours of wash at 37° C. (FIG. 17). These data confirm the initial findings that a dimeric CHP is able to bind to denatured collagens with fast kinetics, high affinity, and without significant workup.

An advantage of the dimeric CHP is that it can be used in vivo with much less significant preparation before use. In current CHPs, it is necessary to perform at least one of several conditioning steps to prime the CHPs for binding to the body (melting to reverse triple-helix formation, UV decaging of sterically limiting agents, etc). Due to the dimeric CHP's quicker folding kinetics and similar binding affinity to gelatin with a lower Tm, no such preparation step is necessary. Since the dimeric CHP has a melting point very close to body temperature, during injection, the ambient temperature of the body is sufficient to reverse any self-folding present in the material, allowing it to readily bind to sites of collagen denaturation in the body. Conversely, current CHPs with similar affinities readily form triple helices which melt at a temperature significantly higher than body temperature, thus requiring the heating step before application in order to make the CHPs available to bind collagen in the body.

REFERENCES

Yu, S. M. Curr. Opin. Chem. Biol. 2013, vol. 17(6): 968-975.
Boudko, S.; Frank, S.; et. al. Nucleation and propagation of the collagen triple helix in single-chain and trimerized peptides: Transition from third to first order kinetics. J. Mol. Biol. 2002, vol. 317: 459-470.
Xu, Y.; Bhate, M.; and Brodsky, B. Characterization of the Nucleation Step and Folding of a Collagen Triple-Helix Peptide. Biochemistry, 2002, vol. 41: 8143-8151.
Ackerman, M. S.; and Brodsky, B. Sequence Dependence of the Folding of Collagen-like Peptides. J. of Biol. Chem. 1999, vol. 274(12): 7668-7673.

We claim:

1. A peptide conjugate comprising
   a) an active agent;
   b) a spacer moiety; and
   c) a dimeric collagen hybridizing peptide comprising
      i) a first and second collagen hybridizing peptide;
      ii) a linker; and
      iii) a branch point,
   wherein the first and second collagen hybridizing peptides comprise the sequence of at least $(GXY)_n$, wherein G is glycine, wherein X and Y are any amino acid, and wherein n is any number between 3 and 12, and
   wherein the first and second collagen hybridizing peptides are capable of forming a triple helix with collagen.

2. The peptide conjugate of claim 1, wherein the first and second collagen hybridizing peptides are identical.

3. The peptide conjugate of claim 1, wherein the first and second collagen hybridizing peptides are different.

4. The peptide conjugate of claim 1, wherein X is proline, modified proline, glutamic acid, or aspartic acid.

5. The peptide conjugate of claim 1, wherein Y is a modified proline, lysine, or arginine.

6. The peptide conjugate of claim 1, wherein a glycine is modified as an Aza-glycine.

7. The peptide conjugate of claim 1, wherein the linker is between the collagen hybridizing peptides and the branch point.

8. The peptide conjugate of claim 1, wherein there are at least two linkers.

9. The peptide conjugate of claim 1, wherein the linker and branch point are on the C-terminal end of the first and second collagen hybridizing peptides.

10. The peptide conjugate of claim 1, wherein the linker and branch point are on the N-terminal end of the first and second collagen hybridizing peptides.

11. The peptide conjugate of claim 1, wherein the linker is one or more glycine residues, aminohexanoic acid, or polyethylene glycol (PEG).

12. The peptide conjugate of claim 1, wherein the branch point attaches to a linker which is attached to the first collagen hybridizing peptide and to a linker which is attached to second collagen hybridizing peptide.

13. The peptide conjugate of claim 1, wherein the branch point is a lysine residue.

14. The peptide conjugate of claim 1, wherein the dimeric peptide comprises the formula (SEQ ID NO: 11)
(Gly-Pro-Hyp)$_6$-Gly-Gly-Gly-Lys.
(Gly-Pro-Hyp)$_6$-Gly-Gly-Gly/

15. The peptide conjugate of claim 1, wherein the dimeric peptide comprises the formula (Gly-Pro-Hyp)₉-Gly-Gly-Gly-Lys.  (SEQ ID NO: 51)

(Gly-Pro-Hyp)₉-Gly-Gly-Gly

16. The peptide conjugate of claim 1, wherein the active agent is a detectable moiety or a therapeutic agent.

17. The peptide conjugate of claim 1, wherein the spacer moiety is between the active agent and the first or second collagen hybridizing peptide.

18. A method of detecting denatured collagen in a sample comprising
   a) contacting a composition comprising the peptide conjugate of claim 1 to a sample, wherein the active agent comprises a therapeutic agent,
   b) detecting the presence or absence of binding of the peptide conjugate to denatured collagen, the presence of binding indicating the presence of denatured collagen in the sample.

19. A method of treating a disease or injury involving collagen damage comprising administering to a subject having a disease or injury involving collagen damage the peptide conjugate of claim 1.

20. A method of screening for a therapeutic agent that treats a disease or injury involving collagen damage comprising
   a) detecting, in a sample, the presence or absence of binding of the peptide conjugate of claim 1 to denatured collagen, the presence of binding indicating the presence of denatured collagen in the sample;
   b) administering to a sample having denatured collagen a composition comprising a peptide conjugate of claim 1 further comprising a therapeutic agent; and
   c) detecting a presence or absence of binding of the peptide conjugate of claim 1 to denatured collagen, the presence of binding indicating the presence of denatured collagen in the sample wherein a decrease in the amount of denatured collagen in the sample detected after administration of the peptide conjugate of claim 1 further comprising a therapeutic agent compared to the amount detected prior to administration of the peptide conjugate of claim 1 further comprising a therapeutic agent indicates a therapeutic agent capable of treating a disease or injury involving collagen damage.

* * * * *